United States Patent [19]

Rapoport et al.

[11] 4,189,583
[45] Feb. 19, 1980

[54] SYNTHESIS OF 4A-ARYL-DECAHYDROISOQUINOLINES

[75] Inventors: Henry Rapoport, Berkeley, Calif.; Dwight D. Weller, Champaigne, Ill.; Richard D. Gless, Oakland, Calif.

[73] Assignee: The United States of America as represented by the Department of Health, Education and Welfare, Washington, D.C.

[21] Appl. No.: 900,275

[22] Filed: Apr. 26, 1978

[51] Int. Cl.$^2$ .................. C07D 211/26; C07D 217/24
[52] U.S. Cl. ..................................... 546/141; 546/192
[58] Field of Search .................... 260/283 SY, 289 D; 546/192, 141

[56] References Cited

U.S. PATENT DOCUMENTS 3,953,434  4/1976  Hauck et al. .................... 260/289 D Primary Examiner—Glennon H. Hollrah
Assistant Examiner—D. B. Springer
Attorney, Agent, or Firm—John S. Roberts, Jr.

[57] ABSTRACT

This invention relates to a process for the production of 4a-aryldecahydroisoquinolines where the aryl group is selected as 3-methoxy phenyl. These compounds are morphine analogs and show utility similar to the known morphine, codeine, and thebaine. In this process particular novelty is asserted for the production of a nipecotic ester ethyl 4-(3'-methoxyphenyl)-1-methyl piperidine-3-carboxylate. Furthermore, novelty is asserted for the step of conversion of the nipecotates through cyclization to cis- or trans-tert-butyl 1,6-dioxo-4a-(3'-methoxyphenyl)-2-methyldecahydroisoquinoline-7-carboxylate, which may also be easily converted to the keto amide, trans-1,6-dioxo-4a-(3'-methoxyphenyl)-2-methyldecahydroisoquinoline.

2 Claims, No Drawings

SYNTHESIS OF 4A-ARYL-DECAHYDROISOQUINOLINES

The present invention relates to a process of 4a-aryl-decahydroisoquinolines (2 and 3) which represent new morphine analogs to develop analgesics possessing less of the undesirable side effects of morphine. This synthesis requires both steric control of the ring juncture and functionality in the carbocyclic (C) ring.

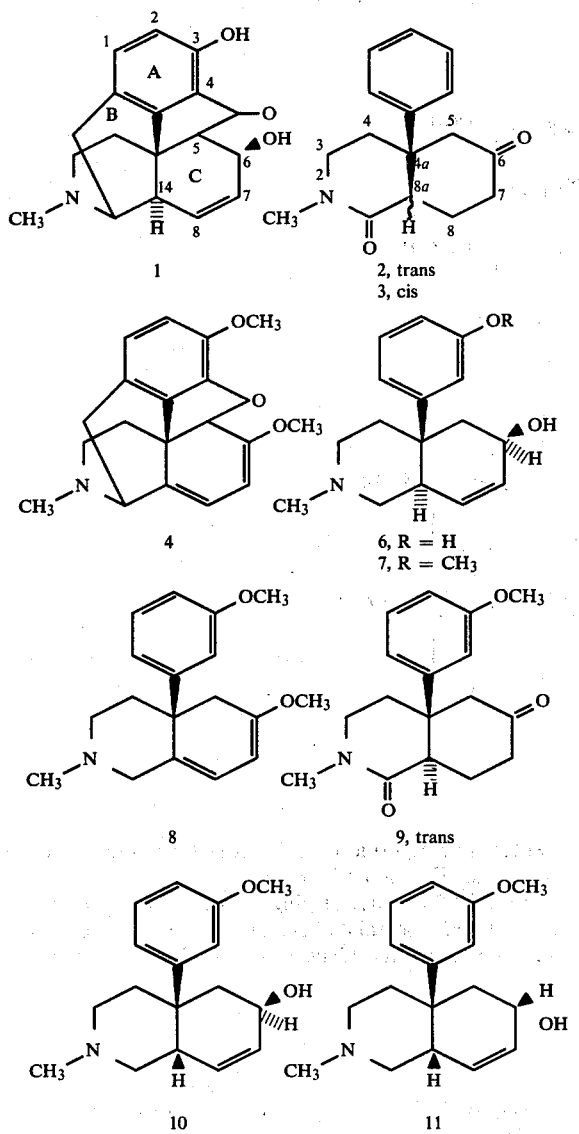

Syntheses are presented of 4a-(3'-methoxyphenyl)-decahydroisoquinolines with the carbocyclic ring functionalized so as to resemble the substitution pattern in ring C of the morphine alkaloids. A versatile synthesis was developed for the starting 4-arylnipecotic acid which was then, via the methylene lactam rearrangement and intramolecular Michael reaction, stereospecifically converted to the 1,6-dioxodecahydroisoquinoline, trans-1,6-dioxo-4a-(3'-methoxyphenyl)-2-methyl-decahydroisoquinoline (keto amide trans-9). Reduction gave ketone trans36 ]trans-4a-(3'-methoxyphenyl)-2-methyl-6-oxodecahydroisoquinoline], and selective functionalization at C-7 led to the key unsaturated ketal, trans-$\Delta^7$-6,6-dimethoxy-4a-(3'-methoxyphenyl)-2-methyl-octahydroisoquinoline (39). Hydrolysis yielded codeinone analog, $\alpha,\beta$-unsaturated ketone 40 [trans-$\Delta^7$-4a-(3'-methoxyphenyl)-2-methyl-6-oxooctahydroisoquinoline], reduction gave codeine analog $\Delta^7$-allylic alcohol 7, and ether cleavage produced the morphine analog, trans-$\Delta^7$-6$\alpha$-hydroxy-4a$\alpha$-(3'-hydroxyphenyl)-2-methyloctahydroisoquinoline (6). Cis-fused analogs were obtained through 9 and ketal amide, 6,6-ethylenedioxy-4a-(3'-methoxyphenyl)-2-methyl-1-oxodecahydroisoquinoline (34) or trans-$\Delta^7$-4a-(3'-methoxyphenyl)-2-methyl-6-oxooctahydroisoquinoline (40) via isomerization at C-8a and were the predominant isomers at equilibrium. Alkali- or acid-catalyzed elimination of methanol from $\Delta^7$-dimethyl ketal 39 produced mainly the thebaine analog, $\Delta^6$, $\Delta^{8(8a)}$-6-methoxy-4a-(3'-methoxyphenyl)-2-methylhexahydroisoquinoline (8), which could be hydroxylated at C-8a with peracid to 14-hydroxycodeinone analogs, $\Delta^7$-8a-hydroxy-4a-(3'-methoxyphenyl)-2-methyl-6-oxooctahydroisoquinolines (57 and 58), but would not participate in Diels-Alder cycloaddition with a variety of dienophiles.

In an earlier article, Weller and Rapoport, J. of the Am. Chem. Soc., 98:6650 (1976), it was shown that trans- and cis-4a-phenyldecahydroisoquinolines (2 and 3) could be prepared but the problem remained of the proper concordance of a different aryl fraction than phenyl as well as the concordance in the C ring, thus decahydroisoquinolines were necessary whose C rings would, with the exception of the C-5 oxygen bridge linkage, mimic the C rings of the hydrophenanthrene opium alkaloids. In order to prepare compounds which were pharmacologically consonant with natural compounds, the 4a-aryl moiety was chosen to be 3-methoxyphenyl. Thus, in the present system, decahydroisoquinolines 6, 7, 8 analogs of morphine, codeine, and thebaine 4 were prepared from a ketoamide, trans-1,6-dioxo-4a-(3'-methoxyphenyl)-2-methyldecahydroisoquinoline (trans-9). In addition, although trans-9 possesses the trans ring fusion, the present synthesis allows for both a trans- and cis- material, including the epimeric cis codeine analogs 10 and 11 (cis-$\Delta^7$-6$\alpha$- and cis-$\Delta^7$-6$\beta$-hydroxy-4a$\alpha$-(3'-methoxyphenyl)-2-methyloctahydroisoquinolines).

In the plan of the present synthesis of the compounds, the synthesis of the keto amide above required the correct nipecotic ester and previous processes for the production of the nipecotates were unuseable.

PRIOR ART STATEMENT

Dwight D. Weller and Henry Rapoport, J. of the Am. Chem. Soc., 98:6650 (1976).

Dwight D. Weller, Richard D. Gless, and Henry Rapoport, J. of Organic Chemistry, 42:1485 (1977).

UTILITY STATEMENT

Members of the group of compounds embodied in this process, including intermediates, have shown morphine agonist usefulness mimicing the closely structured morphine, codeine, and thebaine. Others have morphine antagonist activity. Additionally, the reduction of the amide function, as, e.g., in trans-1,6-dioxo-4a-(3'-methoxyphenyl)-2-methyldecahydroisoquinoline (trans-9) and trans- and cis-6,6-ethylenedioxy-4a-(3'-methoxyphenyl)-2-methyl-1-oxodecahydroisoquinoline (34), serves to potentiate the activity.

FORMATION OF DECAHYDROISOQUINOLINES

The synthesis of keto amide 9 required the nipecotic ester, ethyl 4-(3'-methoxyphenyl)-1-methylpiperidine-3-carboxylate (23). In the 1976 *J. of the Am. Chem. Soc.* article, ante, was reported a general synthesis of 4-aryl 2-substituted nipecotates, but this was unsuccessful for the very important 2-unsubstituted derivatives.

The present process involves a Michael addition to cinnamates:

ester, ethyl 4-(3'-methoxyphenyl)-2-piperidone-5-carboxylate (21), via standard procedures. Selective reduction of the amide function of 21 was achieved by reaction with trimethyloxonium fluoroborate followed immediately by treatment with NaBH$_4$ in ethanol to yield amino ester, ethyl 4-(3'-methoxyphenyl)-piperidine-3-carboxylate (22). Reductive methylation gave the required nipecotate 23 in 48% overall yield from 3-methoxybenzaldehyde (18).

The conversion of nipecotate 23 into the intermediate 4-carboxymethyl-4-(3'-methoxyphenyl)-1-methyl-3-

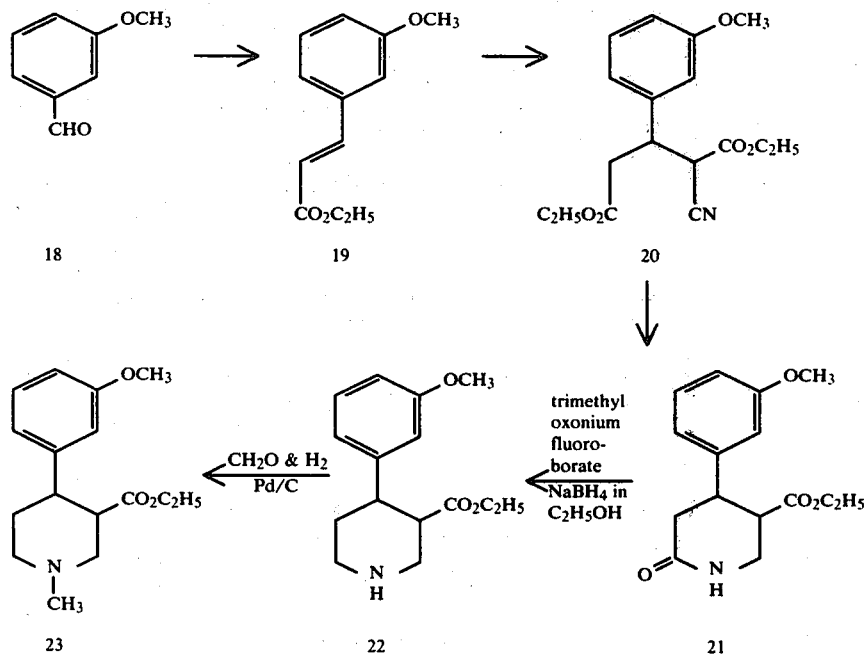

In the preparation of ethyl 4-(3'-methoxyphenyl)-1-methylpiperidine-3-carboxylate (23), a synthesis of 4-aryl 2-unsubstituted nipecotic acids was developed. In this process modifying a known procedure [cf. C. F. Koelsch, *J. of the Am. Chem. Soc.*, 65:2459 (1943)], 3-methoxybenzaldehyde (18) was converted to the amide methylene-2-piperidone (29) followed the previous Weller and Rapoport process, *J. of the Am. Chem. Soc.*, 98:6650 (1976), ante, relying on the methylene lactam arrangement, selenium dioxide oxidation and allylic rearrangement, and Claisen rearrangement below:

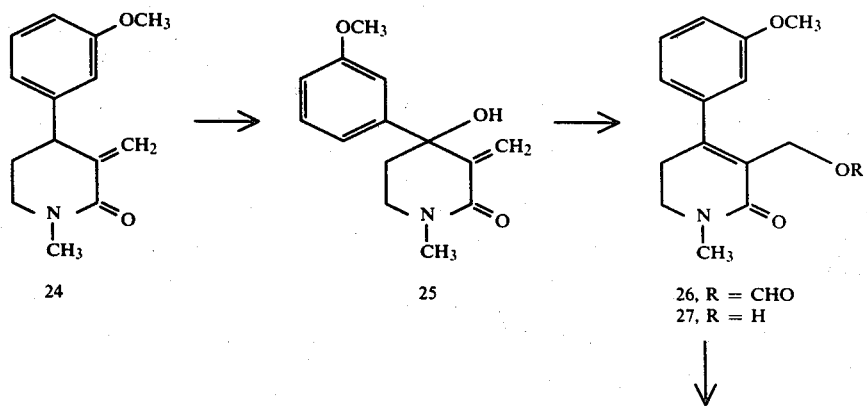

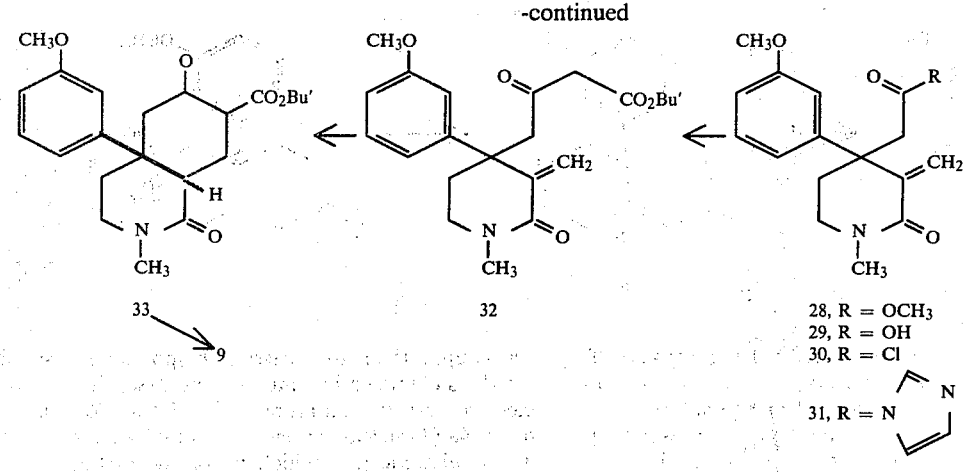

28, R = OCH₃
29, R = OH
30, R = Cl
31, R = N⌒N

The next step of conversion of 4-carboxymethyl-4-(3'-methoxyphenyl)-1-methyl-3-methylene-2-piperidone (29) →9 is believed original. The problem faced was that it was necessary to introduce another carbon atom and close the carbocyclic ring C. To achieve this chain extension and produce a carbanionic center for conjugate addition to the methylene lactam, the carboxymethyl residue was converted to a β-keto ester.

A superior method was found in conversion of acid 29 to imidazolide 31 by the action of carbonyldiimidazole in CHCl₃/THF and reaction with the malonate reagent, resulting in a quantitative yield of very pure β-keto ester, tert-butyl 4-[4'-[4'-(3''-methoxyphenyl)-1'-methyl-3'-methylene-2'-oxopiperidyl]]-3-oxobutyrate (32) suitable for direct use in the ring closure step.

The previous cyclization conditions (Et₃N, CH₃OH, 25° C.) (J. Am. Chem. Soc., 98:6650, 1976), when applied to the ring closure of 32 to tert-butyl 1,6-dioxo-4a-(3'-methoxyphenyl)-2-methyl-decahydroisoquinoline-7-carboxylate (33), required long times (2–5 days) and gave substantial amounts (13%) of the cis isomer. Several other alkaline catalyzed procedures were tested (Table 1) and CH₃ONa/CH₃OH proved conveniently rapid and a trans/cis ratio reaching 87/13 was achieved. Isomeric purification may be done at this stage via recrystallization, leaving the oily cis-33 in the mother liquors and returning pure trans-33 in 70% as calculated from 29.

TABLE 1
Cyclization of β-Keto Ester 32 to cis- and trans-4a-(3-Methoxyphenyl)decahydroisoquinoline (33)

| Alkaline catalyst | | | | Yield[c] % | |
|---|---|---|---|---|---|
| Compound | Mol % | Solvent[a] | Time, h[b] | Cis | Trans |
| (C₂H₅)₃N | 200 | CH₃OH | 48–120 | 12 | 88 |
| CH₃ONa | 10 | CH₃OH | 2.75 | 13 | 87 |
| CH₃ONa | 25 | CH₃OH/H₂O, 2/1 | 2 | 13 | 87 |
| (CH₃)₃COK | 10 | (CH₃)₃COH | 1 | 45 | 55 |
| (CH₃)₃COK | 10 | (CH₃)₃COH | 12[d] | 50 | 50 |
| (CH₃)₃COK | 10 | C₆H₅CH₃ | 6 | 25 | 75 |

[a]All reactions carried out at 25° C.
[b]Reactions conducted until completion as indicated by TLC.
[c]Total crude yield was a quantitative mixture of isomers.
[d]Completed after 1 h; additional time for equilibration.

The assignment of stereochemistry and the determination of isomeric purity were performed by hydrolyzing and decarboxylating crude β-keto ester 33 to ketones 9, followed by ketalization of the crude material to give a mixture of ethylene ketals, trans- and cis-6,6-ethylenedioxy-4a-(3'-methoxyphenyl)-2-methyl-1-oxodecahydroisoquinoline (34).

The amide and ketone functions at C-1 and C-6 of trans-9 and cis-9 were reduced as shown below:

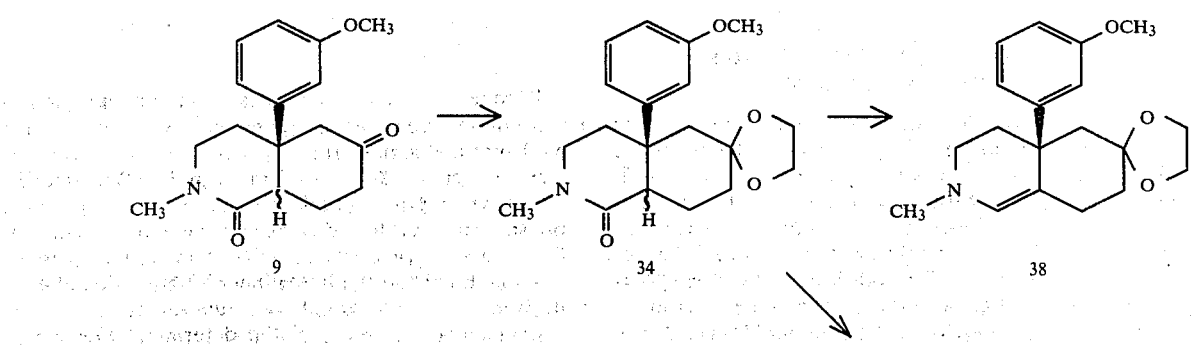

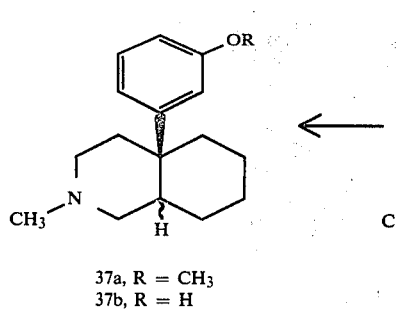

37a, R = CH₃
37b, R = H

36

35

Ether cleavage occurred under the vigorous WolffKishner conditions. The methoxy amines, trans-4a-(3'-methoxyphenyl)-2-methyldecahydroisoquinoline (trans-37a) and cis-4a-(3'-methoxyphenyl)-2-methyldecahydroisoquinoline (cis-37a), were obtained in low yields and the phenols, trans-4a-(3'-hydroxyphenyl)-2-methyldecahydroisoquinoline (trans-37b) and cis-4a-(3'-hydroxyphenyl)-2-methyldecahydroisoquinoline (cis-37b), were the major products. Although the cis materials were oils and formed oily picrates, the NMR of cis-37a was in accord with the reported spectrum of Ripka, Chem. Abstr., 80:95760, 108403 (1974). Amine trans-37a formed a picrate, mp 165°–166° C. while the phenol trans-37b was a solid, mp 210°–211.5° C.

In the above, the compounds illustrating the reduction of the amide were the most interesting, as in 35, 36, 37a, and 37b.

action upon the ketone carried the potential of sacrificing the stereochemical integrity at C-8a, the key intermediate was the unsaturated ketal trans-$\Delta^7$-6,6-dimethoxy-4a-(3'-methoxyphenyl)-2-methyloctahydroisoquinoline (39) which yields the $\alpha,\beta$-unsaturated ketone trans-$\Delta^7$-4a-(3'-methoxyphenyl)-2-methyl-6-oxooctahydroisoquinoline (40) (analogue of codeione) via mild acid hydrolysis. The preference for the cis ring fusion in the decahydroisoquinoline series allows production of conjugate ketone cis-$\Delta^7$-4a-(3'-methoxyphenyl)-2-methyl-6-oxooctahydroisoquinoline (42) and $\beta,\gamma$-unsaturated ketone $\Delta^{8(8a)}$-4a-(3'-methoxyphenyl)-2-methyl-6-oxooctahydroisoquinoline (41) under equilibrating conditions. Additionally, 39 was an ideal candidate for the preparation of dienol ether $\Delta^6$, $\Delta^{8(8a)}$-6-methoxy-4a-(3'-methoxyphenyl)-2-methylhexahydroisoquinoline (8) (thebaine analog) via loss of methanol.

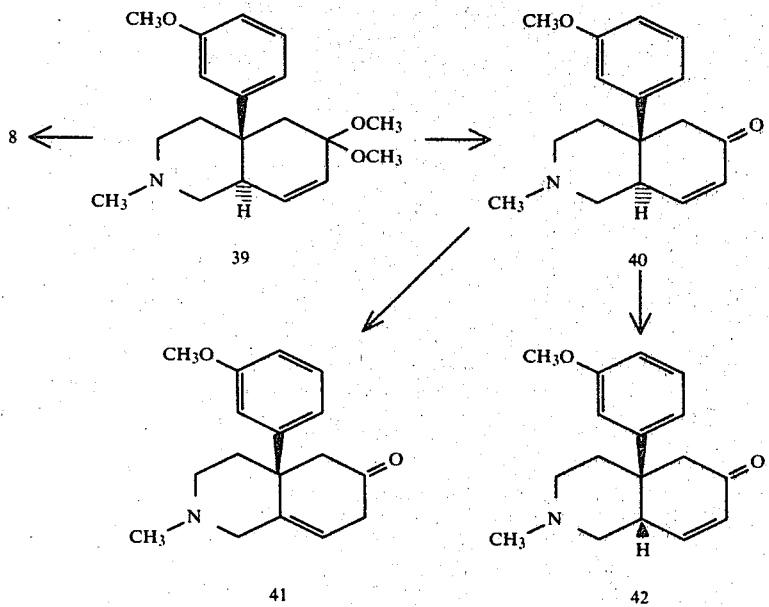

FUNCTIONALIZATION OF THE CARBOCYCLIC RING

The prime consideration in the construction of the decahydroisoquinoline C-ring analogs of the morphine alkaloids was the incorporation of functionality sufficient to allow for formation of both the C-6 oxygen function and the $\Delta^7$-ene and $\Delta^{6,8(8a)}$-diene. The route to these derivatives inherently produced the C-6 ketone and thus the problem of introducing the remaining unsaturation was formally reduced to converting an one to an enone and thence to a dienol ether. Since direct Ketone trans-36 [trans-4a-(3'-methoxyphenyl)-2-methyl-6-oxodecahydroisoquinoline] was ketalized in methanol containing trimethyl orthoformate and treatment of crude ketal 44 [trans-6,6-dimethoxy-4a-(3'-methoxyphenyl)-2-methyldecahydroisoquinoline] with phosphorus oxychloride and pyridine in toluene afforded a 91% yield of enol ethers, trans-$\Delta^6$- and trans-$\Delta^5$-6-methoxy-4a-(3'-methoxyphenyl)-2-methyloctahydroisoquinolines (45a and 46a), in an 83/17 ratio. The assignment of structure and the determination of the isomeric purity were done via NMR. The larger $W_{\frac{1}{2}}$ for the vinyl proton of 45a (7 Hz) compared to that of 46a (2 Hz) was taken to reflect the larger coupling expected for the C-7 proton. A similar situation holds for enol acetates 45b and 46b obtained in 79/21 ratio after refluxing with tosic acid and acetic anhydride ($W_{\frac{1}{2}}$ for 45b, 7 Hz; for 46b, 4 Hz). Thus the C-7 enol predominated over the C-5 enol by a synthetically useful margin. Treatment of the enol ether mixture with N-bromoacetamide in methanol (methyl hypobromite) resulted in a clean conversion to the two bromo ketals, trans-7- and trans-5-bromo-6,6-dimethoxy-4a-(3'-methoxyphenyl)-2-methyldecahydroisoquinoline (47 and 48).

PREPARATION OF RING C ANALOGS

To meet the purpose of the present work, an order of first interest was the preparation of close relatives to the morphine alkaloids via the synthesis of unsaturated ketones 40, 41, and 42. With $\Delta^7$-ketal 39 and $\Delta^8$-ketal 49 at hand, the problem remaining was the formation of the cis enone 42. Hydrolysis of 49 produced neopinone analog 41 but 39 afforded a mixture of $\Delta^7$- and $\Delta^8$-enones 40 and 41 (3/1) under the standard hydrolysis conditions (3 N acetic acid, 25° C.). Both 40 and 41 proved stable to the hydrolysis conditions. As the hydrolysis of codeinone dimethyl ketal under the same nonequilibrating conditions produced no neopinone,

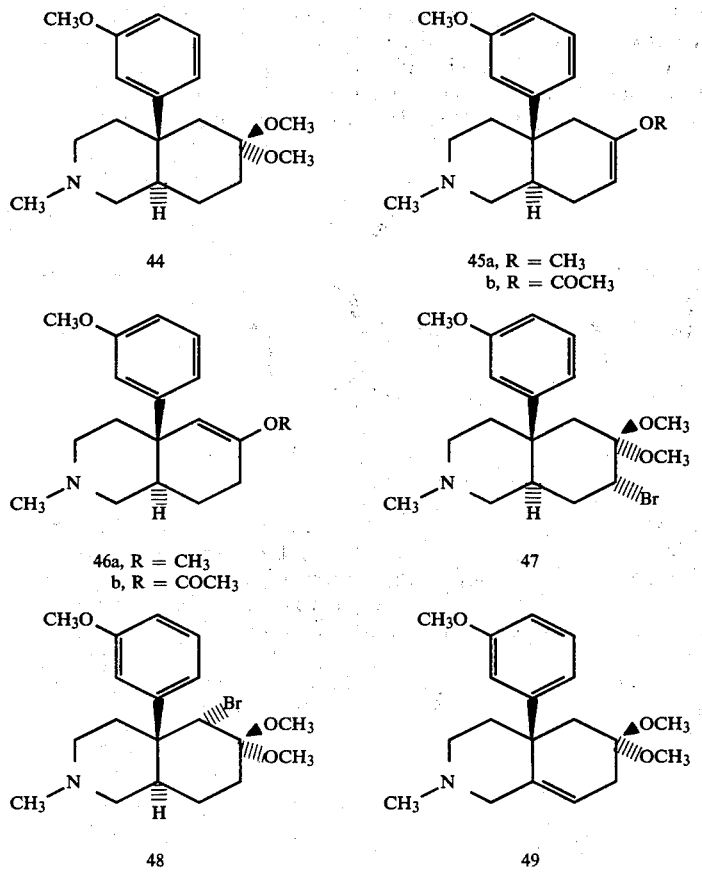

Treatment of the crude mixture of bromo ketals 47/48 with potassium tert-butoxide in Me₂SO at 60° C. resulted in two easily separable materials. Eluted first from silica was 7% of unreacted 48 followed by the unexpected neopinone dimethyl ketal analog $\Delta^{8(8a)}$-6,6-dimethoxy-4a-(3'-methoxyphenyl)-2-methyloctahydroisoquinoline (49) in 74% yield. With the same reagents at 25° C., a 60/40 mixture of $\Delta^7$-ketal 39 and $\Delta^8$-ketal 49 was obtained. Incorporation of tert-butyl alcohol as a cosolvent lead to prolonged reaction times but did not improve the 39/49 ratio while tert-butoxide in refluxing tert-butyl alcohol or tert-amyl alcohol had no effect upon the bromides. Lithium fluoride, chloride, or carbonate in Me₂SO at high temperatures lead to extensive composition. Fortunately, DBN in Me₂SO at 120° C. produced dehydrobromination without rearrangement and returned a 68% yield of $\Delta^7$-ketal 39 after chromatography.

this behavior provided an additional example of the difference between the decahydroisoquinolines and the natural materials caused by the lability in the former of the trans proton at C-5a. After several trails 0.2 N HClO₄ was found to produce the least amount of $\Delta^8$-enone 41 in the hydrolysis (~20%).

The synthesis of the cis $\Delta^7$-enone 42 was performed under equilibrating conditions (CH₃ONa, CH₃OH). Beginning with either ketone 40 or 41, a mixture of 41 and 42 was produced with no detectable trans enone 40. The separation of conjugated and nonconjugated enones was readily accomplished via the bisulfite extraction procedure developed for ketones in the morphine series. The unconjugated ketone 41 could be recovered pure after adjusting the pH of the bisulfite extract to 8.5 since only 1,2-addition to the carbonyl had occurred. The conjugated isomers 40 and 42 remained in the aqueous phase since 1,4-addition of bisulfite had occurred producing a sulfonic acid which was not regenerated via β-elimination until pH 12. Significantly no isomerization occurred in this strongly alkaline medium and both trans and cis enones, 40 and 42, were recovered pure. From the hydrolysis of Δ⁷-trans ketal 39 were obtained 41 (16%) and 40 (62%) after separation while the equilibrating conditions produced 41 (32%) and 42 (57%).

The reduction of β,γ-enone 41 with NaBH₄ in ethanol produced a complex mixture from which was isolated 47% of a chromatographically homogeneous β,γ-unsaturated alcohol. Certain NMR resonances (C-6 H, NCH₃) were broadened and when the unsaturation was reduced with H₂Pt in methanol, a mixture of products was obtained. The two major products were trans axial alcohol, trans-6α-hydroxy-4aα-(3'-methoxyphenyl)-2-methyldecahydroisoquinoline (50), (major) and trans equatorial alcohol, trans-6β-hydroxy-4aα-(3'-methoxyphenyl)-2-methyldecahydroisoquinoline (51), which reflected the isomeric constitution at C-6 of the original unsaturated alcohols.

morphine analog, trans-Δ⁷-6α-hydroxy-4aα-(3'-hydroxyphenyl)-2-methyloctahydroisoquinoline (6) in 60% yield.

The reduction of the cis α,β-unsaturated ketone 42 was complicated by facile saturation of the C-7,8 double bond. Using AlH₃THF as in the reduction of 40, the major product was the saturated ketone cis-36 accompanied by small amounts of unsaturated materials, and borohydride in ethanol produced a complex mixture of saturated and unsaturated alcohols. Diisobutylaluminum hydride in toluene displayed a minimal amount of conjugate reduction, yielding only 9% of 36 along with 68% of cis Δ⁷-allylic alcohols 10 and 11.

In the proof of structure of the alcohols, cis-Δ⁷-6α- and cis-Δ⁷-6β-hydroxy-4aα-(3'-methoxyphenyl)-2-methyloctahydroisoquinolines (10 and 11), the major isomer was assigned structure 10 and the minor isomer was assigned structure 11.

Although thebaine analog 8 was available by the base-catalyzed elimination of CH₃OH from 49, the low yield and the difficulty in obtaining pure material hin-

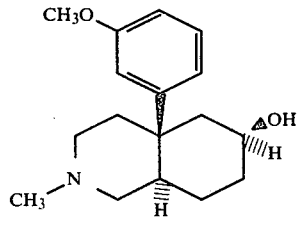

50

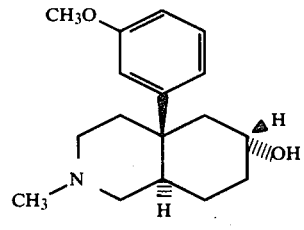

51

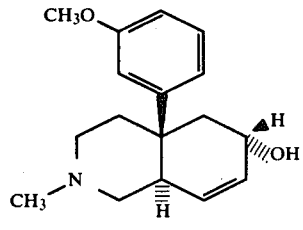

52

The reduction of trans α,β-enone 40 proceeded without incident using AlH₃THF and two allylic alcohols were readily obtainable accompanied by a small amount (5%) of saturated ketone trans-36. The major material (56%) was found to be codeine analog 7 by reduction to axial alcohol 50, while the minor isomer (31%) was converted to equatorial alcohol 51 and thus represented the isocodeine analog 52. Treatment of codeine analog 7 with potassium thioethoxide in DMF yielded the dered its preparation in quantity. A more efficient procedure was the treatment of 39 with POCl₃/pyridine in hot toluene, which cleanly gave CH₃OH elimination with a 75% recovery but produced an 85/15 mixture of dienes 8 and 55. The structure of 55 was readily assigned on the basis of the NMR of the H-5 and H-8 vinyl protons (singlet and triplet). The chromatographic separation of 55 and 8 was not completely efficient.

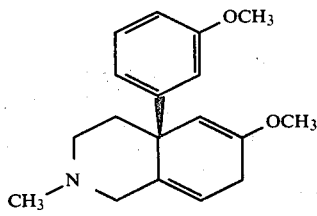

55

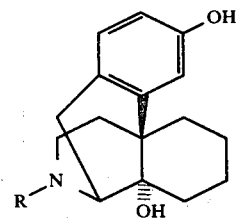

56

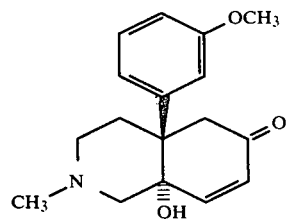

57

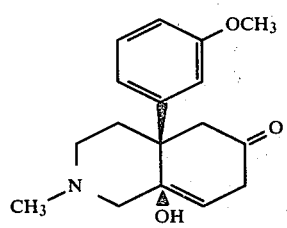

58

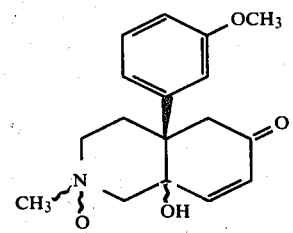

59

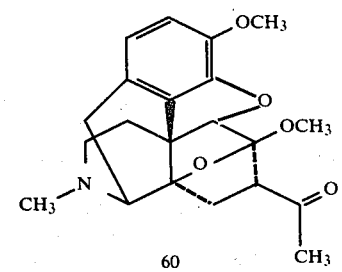

60

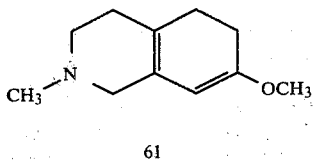

61

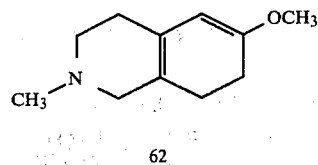

62

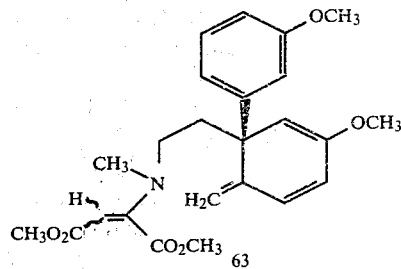

63

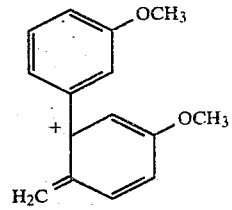

64

The homoannular conjugate diene common to both thebaine (4) and 8 is, in the case of thebaine, a highly reactive system capable of many transformations. Thus, oxidation of 4 with peracid yields 14-hydroxycodeinone [cf. F. M. Hauser, T. K. Chen, and F. I. Carroll, *J. Med. Chem.*, 17:1117 (1974)], which is transformed to the important narcotic antagonist naloxone (U.S. Pat. No. 3,254,088). Simple 14-hydroxymorphinans such as 56 have been prepared and are both potent agonists and antagonists [cf. Monkovic et al, *Can. J. Chem.*, 53:3094 (1975)]. Thus, 14-hydroxylated derivatives in the present decahydroisoquinoline series were prepared. Treatment of 8 with m-chloroperbenzoic acid in a mixture of acetic acid and trifluoroacetic acid at 95° C. returned two materials which were identified as $\Delta^7$-8a-hydroxy-4a-(3'-methoxyphenyl)-2-methyl-6-oxooctahydroisoquinolines (57 and 58) in 50% yield. In addition, a significant amount (14%) of the N-oxide 59 was isolated.

It is postulated that the stereochemistry assignments to 57 and 58 were that the major material (43%) was trans fused and the minor isomer (7%) was the cis material, since reactions performed under kinetically controlled conditions tend to preferentially attack the $\beta$ face of the molecule at C-8a [e.g., the ring closure of 32 to 33 and the hydrogenation of 38 to trans-35 (trans-6,6-ethylenedioxy-4a-(3'-methoxyphenyl)-2-methyldecahydroisoquinoline].

A second important reaction of the thebaine C ring is the facile addition of dienophiles s to give 6,14-etheno bridged species such as 60 (from methyl vinyl ketone) which have been converted into highly potent analgesics [cf. Bentley et al, *J. Am. Chem. Soc.*, 89:3267 (1967)].

Additionally, no products were obtained by reacting under Diels-Alder conditions ethyl acrylate or methyl vinyl ketone where adducts were obtained with compounds 61 and 61. Also a more reactive dimethyl acetylenedicarboxylate (DMAD) formed no cycloadduct but instead the unstable triene 63 was obtained in 45% yield accompanied by other products. The structure of 63 was evident from its NMR (six distinct vinyl protons) and its mass spectral fragmentation, giving 64 as the base peak. The facility with which 8 was cleaved was undoubtedly due to the allylic nature of the bond being broken.

In summary, beginning with the easily obtainable keto amide trans-9 close relatives of the morphine alkaloids possessing both cis and trans ring fusions have been prepared by the present process and in good overall yield. The chemistry of these materials qualitatively resembled that of the natural series but quantitative differences arose owing to the additional features in the morphine skeleton. Thus, enol ether 46 and diene 55 have no counterpart in the alkaloids since enolization toward C-5 is hindered by the 4,5-oxide bridge. Similarly the reduction of codeinone and neopinone and the oxidation of thebaine proceed with exclusive $\beta$-attack due to the extraordinary hindrance of the $\alpha$ face, while their analogs 40, 41, and 8 here give mixtures of epimers in these reactions. Two distinct differences did emerge, namely, the facile isomerization of the double bond from $\Delta^7$ to $\Delta^{8(8a)}$ and the nonreactivity of thebaine analog 8 toward Diels-Alder cycloaddition, giving rise, in the case of DMAD, to the triene 63.

EXAMPLE 1

Ethyl 3-Methoxycinnamate (19)

3-Methoxycinnamic acid was prepared as described by G. Lock and E. Bayer, *Ber.*, 72:1064 (1939), except that $\beta$-picoline was used as solvent. The yield of acid was 100%, mp 118°–120° C. This material, diethyl sulfate (102 g, 0.66 mol), tris(2-hydroxypropyl)amine (151 g, 0.79 mol), and acetone (100 mL) were concentrated on a steam bath for 1.5 h, cooled (25° C.), poured into H$_2$O (1600 mL), and extracted with ether (3 × 800 mL). The combined organic phases were washed with saturated NaHCO$_3$ (800 mL) and saturated NaCl (800 mL), dried, evaporated, and distilled, affording 120 g (88%) of the cinnamate: bp 96°–101° C. (0.1 mm); NMR $\delta$ 7.72 (d, J=16 Hz, 1H), 7.17 (m, 4H), 6.46 (d, J=16 Hz, 1H), 4.30 (q, J=7 Hz, 2H), 3.83 (s, 3H), 1.38 (t, J=7 Hz, 3H).

EXAMPLE 2

Diethyl 2-Cyano-3-(3'-methoxyphenyl)pentanedioate (20)

Michael addition with ethyl cyanoacetate was carried out as in J. F. Thorpe and W. Udall, *J. Chem. Soc.*, 75:904 (1899) for the phenyl case, giving a 93% yield of 20; bp 150°-160° C. (0.3 mm); NMR δ 7.42-6.66 (m, 4H), 4.25-3.79 (m, 6H), 3.79 (s, 3H), 2.90 (m, 2H), 1.21 (t,J=7 Hz, 3H), 1.15 (t,J=7 Hz, 3H); IR (neat) 2235, 1725 cm$^{-1}$; mass spectrum m/e (rel intensity) 319 (30), 245 (73), 161 (100). Anal. Calcd for $C_{17}H_{21}NO_5$: C, 63.9; H, 6.6; N, 4.4. Found: C, 64.1; H, 6.6; N, 4.5.

EXAMPLE 3

Ethyl 4-(3'-Methoxyphenyl)-2-piperidone-5-carboxylate (21)

The adduct diethyl 2-cyano-3-(3'-methoxyphenyl)-pentanedioate (20) (30.2 g, 92.7 mmol), $PtO_2$ (1.5 g), ethanolic HCl (12 N. 31.5 mL, 0.38 mol), and ethanol were shaken under $H_2$ (33-49 psi) for 7 h. The residue after filtration and evaporation was dissolved in $CHCl_3$ (100 mL), washed with saturated $NaHCO_3$ (200 mL), dried, and evaporated. After addition of toluene (200 mL) the solution as refluxed for 1 h and the solvent removed to give 26.67 g (100%) of crude amide as a mixture of isomers. On crystallization from $CH_2Cl_2$/hexane a single isomer was obtained: mp 144°-145.5° C.; NMR δ 7.20 (m, 2H), 6.8 (m, 3H), 4.14 (q,J=7 Hz, 2H), 3.83 (s, 3H), 3.8-3.3 (m, 3H), 3.17 (m, 1H), 2.87 (d,J=5 Hz, 2H), 1.23 (t,J=7 Hz, 3H); IR (KBr) 1735, 1665 cm$^{-1}$; mass spectrum m/e (rel intensity) 277 (41), 134 (100). Anal. Calcd for $C_{15}H_{19}NO_4$: C, 65.0; H, 6.9; N, 5.0. Found: C, 65.1; H, 6.8; N, 5.02.

EXAMPLE 4

Ethyl 4-(3'-Methoxyphenyl)piperidine-3-carboxylate (22)

To a solution of trimethyloxonium fluoroborate (14.78, 99 mmol) in $CH_2Cl_2$ (250 mL) was added a 24.9 g portion of the crude amide obtained in Example 3. After 43 h at 25° C. the solvent was evaporated, and the residue was dissolved in ethanol (250 mL), cooled (−10° C., internal) and treated portionwise with $NaBH_4$ (10.2 g, 0.27 mol, 20 min) with vigorous mechanical stirring while maintaining the solution at 5°-10° C. The solution was stirred for 24 h (25° C.), $H_2O$ (250 mL) was added, and the mixture was concentrated and acidified (pH 1) with 1.5 N HCl, neutralized with saturated $NaHCO_3$ (pH 8), and extracted with $CHCl_3$ (3×200 mL). The combined organic extracts were dried, evaporated, and distilled, yielding 14.47 g (61% from 20) of amine 22; bp 110°-130° C. (0.3 mm); NMR δ 7.27 (m, 1H), 6.80 (m, 3H), 3.93 (q,J=7 Hz, 2H), 3.79 (s, 3H), 1.99 (s, 1H), 0.99 (t,J=7 Hz, 3H); IR (neat) 3350, 1725 cm$^{-1}$; mass spectrum m/e (rel intensity) 263 (35), 190 (30), 129 (37), 57 (100), 56 (72). Anal. Calcd for $C_{15}H_{21}NO_3$: C, 68.4; H, 8.0; N, 5.3. Found: C, 68.4; H, 8.0; N, 5.2.

EXAMPLE 5

Ethyl 4-(3'-Methoxyphenyl)-1-methylpiperidine-3-carboxylate (23)

A suspension of the amine of Example 4 (12.27 g, 44.7 mmol), 37% aqueous $CH_2O$ (15 mL, 0.2 mol), 10% Pd/C (1.75 g), and ethanol (100 mL) were shaken for 12 h under $H_2$ (50 psi). The reaction mixture was filtered, evaporated, and distilled, giving 12.05 g of ethyl 4-(3'-methoxyphenyl)-1-methylpiperidine-3-carboxylate (23) (94.5%); bp 130°-140° C. (0.3 mm); NMR δ 7.14 (m, 1H), 6.75 (m, 3H), 3.86 and 3.93 (isomeric quartets, J=7 and 8 Hz, 2H), 3.69 (s, 3H), 3.28 and 3.33 (isomeric sinlets, 3H), 1.03 and 0.95 (isomeric triplets, J=7 and 8 Hz, 3H); IR (neat) 1725 cm$^{-1}$; mass spectrum m/e (rel intensity 277 (31), 276 (10), 71 (37), 70 (50), 44 (100). Anal. Calcd for $C_{16}H_{23}NO_3$: C, 69.3; H, 8.4; N, 5.0. Found: C, 69.2; H, 8.2; N, 5.0.

EXAMPLE 6

4-(3'-Methoxyphenyl)-1-methyl-3-methylene-2-piperidione (24)

The ester ethyl 4-(3'-methoxyphenyl)-1-methylpiperidine-3-carboxylate (23)(5.0 g, 17.5 mmol), NaOH (1.49 g, 35 mmol), $CH_3OH$ (50 mL), and $H_2O$ (25 mL) were refluxed for 5 h. After the thorough removal of solvents, the residue was mixed with acetic anhydride (50 mL) and refluxed for 1 h, then cooled and evaporated and the crude reaction product partitioned between $CHCl_3$ (50 mL) and saturated $NaHCO_3$ (50 mL, pH 8). The aqueous layer was extracted with $CHCl_3$ (2×50 mL) and the combined organic phases dried and evaporated. Distillation gave 3.77 g (92%) of 4-(3'-methoxyphenyl)-1-methyl-3-methylene-2-piperidone (24). Recrystallization ($CH_3Cl_2$/hexane) gave the analytical sample: mp 67°-70° C: NMR δ 7.29 (m, 1H), 6.82 (m, 3H), 6.40 (t,J=2 Hz, 1H), 5.07 (t,J=2 Hz, 1H), 3.75 (s, 3H), 3.34 (m, 2H), 3.04 (s, 3H), 2.17 (m, 2H); IR (KBr) 1645, 1600 cm$^{-1}$; mass spectrum m/e (real intensity) 231 (100), 216 (13). Anal. Calcd for $C_{14}H_{17}NO_2$: C, 72.7; H, 7.4; N, 6.1. Found: C, 72.6; H, 7.3; N, 6.0.

EXAMPLE 7

4-Hydroxy-4-(3'-methoxyphenyl)-1-methyl-3-methylene-2-piperidone (25)

Methylene lactam (24)(633 mg, 2.68 mmol), $SeO_2$ (228 mg, 2.06 mmol), and chlorobenzene (8 mL) were heated at 100° C. for 50 min. Filtration, evaporation, and chromatography ($SiO_2$, $CHCl_3$/$CH_3OH$, 99/1) gave 575 mg (86%) of the tertiary alcohol(25) mp 127°-128° C. from benzene; NMR δ 7.5-6.7 (m, 4H), 6.41 (d,J=7 Hz, 1H), 5.43 (d,J=2 Hz, 1H), 4.18 (bs, 1H), 3.80 (s, 3H), 3.8-3.0 (m, 2H), 2.95 (s, 3H), 2.10 (m, 2H); IR (KBr) 3350, 1640, 1585 cm$^{-1}$; mass spectrum m/e (rel intensity) 247 (100), 230 (20), 229 (11), 228 (13), 112 (92). Anal. Calcd for $C_{14}H_{17}NO_3$: C, 68.0; H, 6.9; N, 5.7. Found: C, 68.2; H, 6.9; N, 5.6.

EXAMPLE 8

3-Formyloxymethyl-4-(3'-methoxyphenyl)-1-methyl-5,6-dihydro-2-pyridone (26)

The tertiary alcohol of Example 7 (254 mg, 1.04 mmol) was solvolyzed in 97% $HCO_2H$ (10 mL) for 16 h at 25° C. and the solvent evaporated. The residue was dissolved in $CHCl_3$ (15 mL) and washed with saturated $NaHCO_3$ (15 mL), the aqueous layer was extracted with $CHCl_3$ (2×15 mL), and the combined organic phases were dried and evaporated to yield 288 mg (100%) of the formate. Distillation [155°-165° C. (0.07 mm)] and recrystallization (benzene/hexane) gave a solid: mp 87°-88° C.; NMR 8.08 (s, 1H), 7.26 (m, 1H), 6.80 (m, 3H), 4.88 (s, 2H), 3.80 (s, 3H), 3.53 (t,J=7 Hz, 2H), 3.07 (t,J=7 Hz, 2H), IR 1700, 1656, 1610 cm$^{-1}$; mass spectrum m/e (rel intensity) 275 (221), 246 (75), 230 (52), 229 (100). Anal. Calcd for $C_{15}H_{17}NO_4$: C, 65.4; H, 6.2; N, 5.1. Found: C, 65.5; H, 6.1; N, 5.0.

EXAMPLE 9

3-Hydroxymethyl-4-(3'-methoxyphenyl)-1-methyl-5,6-dihydro-2-pyridone (27)

Methylene lactam of Example 6 (4.78 g, 20.3 mmol), $SeO_2$ (1.69 g, 15.2 mmol), and chlorobenzene (50 mL) were heated at 100° C. for 1 h, cooled, filtered, and evaporated. The crude alcohol was dissolved in 97% $HCO_2H$ (50 mL) and stirred at 25° C. for 27 h, and formate of Example 8 was isolated as above. The crude formate was dissolved in $CH_3OH$ (50 mL), $K_2CO_3$ (1.42 g, 10.3 mmol) was added, and after 1.5 h at 25° C. the mixture was evaporated and the residue partitioned between $CHCl_3$ (50 mL) and saturated NaCl (50 mL). The aqueous layer was extracted with $CHCl_3$ (2×50 mL), and the combined organic phases dried and evaporated to give 4.50 g (90% overall) of pure allylic alcohol 27 which crystallized upon standing. This product was used directly in the following Claisen rearrangement. Recrystallization (benzene/hexane) gave material of mp 81°–83° C.: NMR δ 7.18 (m, 1H), 6.74 (m, 3H), 4.10 (s, 2H), 3.66 (s, 3H), 3.35 (t,J=7 Hz, 2H), 3.17 (bs, 1H), 2.90 (s, 3H), 2.53 (t,J=7 Hz, 2H); Ir (KBr) 3400, 1655, 1600 $cm^{-1}$; mass spectrum m/e (rel intensity) 247 (3), 230 (2), 229 (7), 44 (100). Anal. Calcd for $C_{14}H_{17}NO_3$: C, 68.0; H, 6.9; N, 5.7. Found: C, 68.0; H, 6.8; N, 5.6.

EXAMPLE 10

4-Methoycarbonylmethyl-4-(3'-methoxyphenyl)-1-methyl-3-methylene-2-piperidone (28)

The allylic alcohol 27 of Example 9 (1.22 g, 4.96 mmol), trimethyl orthoacetate (5.52 g, 46 mmol), and pivalic acid (25 mg, 0.50 mmol) were placed in diglyme (25 mL) and refluxed at 155°–160° C. (internal) with fractionation to remove $CH_3OH$. After 18 h the solvents were evaporated and the residue distilled [bp 175°–185° C. (0.15 mm)] to return 1.21 g (80%) of methyl ester 28. Upon standing the ester crystallized: mp 85°–86° C.; NMR δ 7.30 (m, 1H), 6.86 (m, 4H), 6.65 (s, 1H), 5.57 (s, 1H), 3.76 (s, 3H), 3.47 (s, 3H), 3.17 (m, 3H), 2.87 (s, 4H), 2.53 (m, 2H); IR 1733, 1653, 1595 $cm^{-1}$; mass spectrum m/e (rel intensity) 303 (38), 230 (100). Anal. Calcd for $C_{17}H_{21}NO_4$: C, 67.3; H, 7.0; N, 4.6. Found: C, 67.2; H, 7.0; N, 4.6.

EXAMPLE 11

4-Carboxymethyl-4-(3'-methoxyphenyl)-1-methyl-3-methylene-2-piperidone (29)

To methyl ester 28 of Example 10 (1.20 g, 3.97 mmol) dissolved in $CH_3OH$ (5 mL, 0° C.) was rapidly added KOH (775 mg, 11.9 mmol) in 5 mL of 1/1 $CH_3OH/H_2O$. After 20 h at 25° C., $CHCl_3$ (20 mL) and $H_2O$ (20 mL) were added, the separated aqueous layer was extracted with $CHCl_3$ (20 mL) and the combined organic phases were dried and evaporated to give 178 mg (20%) of 1,3-dimethyl-4-(3'-methoxyphenyl)-2-pyridone (this arises from unreacted allylic alcohol under the alkaline hydrolysis conditions): NMR δ 7.20 (m, 2H), 6.86 (m, 3H), 6.07 (d,J=7 Hz, 1H), 3.81 (s, 3H), 3.57 (s, 3H), 2.10 (s, 3H): IR (neat) 1640 $cm^{-1}$ (broad); mass spectrum m/e (rel intensity) 229 (63), 228 (100). Anal. Calcd for $C_{14}H_{15}NO_2$: C, 73.3; H, 6.6; N, 6.1. Found: C, 73.0; H, 6.6; N, 6.1.

The pH of the aqueous layer was adjusted to 1, the solution was extracted with $CHCl_3$ (3×15 mL), and the combined organic extracts were dried and evaporated to yield 29 (884 mg, 77%); mp 177°–178° C. ($CHCl_3$/hexane); NMR δ 9.4 (bs, 1H), 7.23 (m, 1H), 6.86 (m, 3H), 6.59 (s, 1H), 5.59 (s, 1H), 3.76 (s, 3H), 3.18 (m, 2H), 2.92 (s, 5H), 2.62 (m, 2H); Ir (KBr) 1720, 1645, 1590 $cm^{-1}$; mass spectrum m/e (rel intensity) 289 (32), 230 (100). Anal. Calcd for $C_{16}H_{19}NO_4$: C, 66.4; H, 6.6; N, 4.8. Found: C, 66.2; H, 6.6; N, 5.2.

EXAMPLE 12 tert-Butyl 4-[4'-[4'-(3''-Methoxyphenyl)-1'-methyl-3'-methylene-2'-oxopiperidyl]]-3-oxobutyrate (32)

A. Via tert-Butyl Lithioacetate and 4-Chlorocarbonylmethyl-4-(3'-methoxyphenyl)-1-methyl-3-methylene-2-piperidone (30). Thionyl chloride (9.16 g, 77 mmol) in $CH_2Cl_2$ (100 mL) was cooled (−70° C.) and the acid 29 of Example 11 (5.78 g, 20 mmol) was added at a rate of 2 mL/min. After addition, the bath was removed, the solution allowed to warm to 25° C. (1 h), and the volatiles evaporated. Benzene (100 mL) was added and evaporated and the residual 30 used immediately. NMR δ 7.27 (m, 1H), 6.80 (m, 4H), 5.53 (s, 1H), 3.78 (s, 3H), 3.52 (s, 2H), 3.21 (t,J=6 Hz, 2H), 2.87 (s, 3H), 2.51 (bt, J=6 Hz, 2H): IR (neat) 1800, 1640 1600 $cm^{-1}$.

To THF (33 mL) and 2,2,6,6-tetramethylpiperidine (5.78 g. 41 mmol) at −78° C. was added n-butyllithium (16.4 mL, 2.5 M in hexane, 41 mmol). After 5 min tert-butyl acetate (2.38 g, 20.5 mmol) was added dropwise followed 10 min later by the acid chloride 30 in THF (40 mL) at a rate of 2 mL/min. The solution was maintained at −78° C. for 15 min and then the reaction was quenched by addition of saturated $NH_4Cl$ (55 mL) followed by slowly warming the slurry at 25° C., separating the layers, and washing the aqueous phase with ether (2×40 mL). The combined ethereal layers were washed with 1 N HCl (20 mL) and saturated NaCl (20 mL), dried, and evaporated to give 6.92 g (90%) of crude β-keto ester 32. Chromatography ($SiO_2$, $CHCl_3$/acetone, 3/1) returned 3.5 g (45%) of pure 32.

B. Via the Acid Chloride 30 above and the Magnesium Enolate of tert-Butyl Hydrogen Malonate. Acid chloride formation as above followed by treatment with the magnesium enolate and isolation as below yielded 59% of pure 32 after chromatography.

C. Via the Imidazolide 31 and the Magnesium Enolate of tert-Butyl Hydrogen Malonate. To carbonyldiimidazole (365 mg, 2.2 mmol) dissolved in 20 mL of THF was added acid 29 of Example 11 (578 mg, 2 mmol) in 20 mL of $CHCl_3$. After 60 min at 25° C. the clear solution was evaporated, and the residue dissolved in benzene (20 mL), reevaporated, and redissolved in THF (10 mL). Independently $LiO_2C-CH_2CO_2C_4H_9$ (895 mg, 5.4 mmol) in 20 mL of THF was treated dropwise with isopropylmagnesium bromide (5.2 mmol, 6.65 mL of 0.78 N in THF) giving a pale yellow solution which was heated on a steam bath until precipitation of LiBr was complete. To the heterogeneous magnesium enolate solution was added the solution of crude imidazolide and the suspension was stirred for 16 h. The mixture was poured into $Et_2O$ (25 mL), saturated NaCl (25 mL), and 2 N HCl (10 mL). The separated aqueous layer was washed with $Et_2O$ (2×10 mL) and the combined organic phases were washed with saturated NaCl (10 mL), dried, mixed with benzene (20 mL), and evaporated. The residue was taken up in benzene (50 mL), washed with saturated $NaHCO_3$ (2×10 mL) and saturated NaCl (10 mL), dried, and evaporated to give β-keto ester 32 (789 mg, 100%) as a colorless oil. Chromatography (SiO$_2$, CHCl$_3$/acetone, 3/1) returned 697 mg (90%) of pure 32: NMR δ 7.30 (m, 1H), 6.88 (m, 3H), 6.60 (s, 1H), 3.82 (s, 3H), 2.90 (s, 3H), 1.47 (s, 9H): IR 1720, 1645, 1600 cm$^{-1}$.

EXAMPLE 13 tert-Butyl 1,6-Dioxo-4a-(3'-methoxyphenyl)-2-methyldecahydroisoquinoline-7-carboxylate (33)

In the same manner as above, acid 29 of Example 11 (8.67 g, 30 mmol) was converted to crude β-keto ester 32 of Example 12 (11.5 g, 100%) which was treated with CH$_3$OH (300 mL) containing CH$_3$ONa (3 mmol) for 7 h, then poured into saturated NaCl (400 mL) and benzene (500 mL). The aqueous phase was washed with benzene (3×100 mL) and the combined organic layers were dried and evaporated. The crystalline residue was dissolved in boiling benzene (20 mL), hot hexane (200 mL) was added, then the solution was concentrated to 80 mL and cooled (25° C.) to give 8.03 g (70%) of pure β-keto ester trans-33: mp 159°–161° C.; NMR δ 7.22 (m, 1H), 6.78 (m, 3H), 3.78 (s, 3H), 2.93 (s, 3H), 1.49 (s, 9H); IR 1650, 1629 cm$^{-1}$; mass spectrum m/e (rel intensity) 387 (1), 331 (5), 287 (16), 59 (100). Anal. Calcd for C$_{22}$H$_{29}$NO$_5$: C, 68.1; H, 7.5; N, 3.6. Found: C, 68.0; H, 7.5; N, 3.6.

Chromatography (SiO$_2$, CHCl$_3$/acetone, 9/1) of the mother liquors returned 2.73 g (24%) of a 3/1 mix of β-keto esters cis- and trans-33. Isomeric compositions were determined by hydrolysis, decarboxylation, and ketalization as described below (see Example 16. Likewise 32 (Example 12) was cyclized to 33 as shown in Table 1 of this specification. In all cases the recovery of cyclized material was quantitative and isomer ratios were determined as below (Example 16).

EXAMPLE 14 trans-1,6-Dioxo-4a-(3'-methoxyphenyl)-2-methyl-decahydroisoquinoline (trans-9)

The cyclic β-keto ester trans-33 (Example 13) (3.5 g, 9 mmol) in benzene (50 mL) was treated with TFA (50 mL) at 25° C. After 3 h the solvents were removed, and the residue was taken up in 200 mL of toluene and refluxed for 60 min. Evaporation gave a residue which was recrystallized (benzene/hexane) to yield 2.1 g (81%) of pure trans-9: mp 156°–158° C.,; NMR δ 7.20 (m, 1H), 6.75 (m, 3H), 3.72 (s, 3H), 290 (s, 3H); IR (KBr) 1705, 1635 cm$^{-1}$; mass spectrum m/e (rel intensity) 287 (61), 57 (94), 55 (100). Anal. Calcd for C$_{17}$H$_{21}$NO$_3$: C, 71.0; H, 7.4; N, 4.9. Found: C, 70.8; H, 7.4; N, 4.9.

EXAMPLE 15 trans-6,6-Ethylenedioxy-4a-(3'-methoxyphenyl)-2-methyl-1-oxodecahydroisoquinoline (trans-34)

To a solution of ketone trans-9 of Example 14 (86.1 mg, 0.3 mmol) in benzene (20 mL) were added TsOH.H$_2$O (19.2 mg) and ethylene glycol (56 μL, 1 mmol) and the solution heated with removal of 15 mL of cloudy solvent. Cooling to 25° C., pouring into 5% Na$_2$CO$_3$ (10 mL), washing the organic phase with saturated NaCl (5 mL), drying, and evaporating gave 105 mg (100%) of crude 34. Recrystallization (benzene/hexane, 1:6) gave 91 mg (92%) of pure trans-34: mp 180°–181° C.; NMR δ 7.1 (m, 1H), 6.7 (m, 3H), 3.9–3.6 (m, 7H), 3.65 (s, 3H); 2.67 (s, 3H); IR 1623 (s), 1600 (sh), 1575 cm$^{-1}$; mass spectrum m/e (rel intensity) 331 (79), 232 (57), 99 (100). Anal. Calcd for C$_{19}$H$_{25}$NO$_4$: C, 68.9; H, 7.6; N, 4.2. Found: C, 68.6; H, 7.5; N, 4.4.

EXAMPLE 16 cis-6,6-Ethylenedioxy-4a-(3'-methoxyphenyl)-2-methyl-1-oxodecahydroisoquinoline (cis-34)

Ketal trans-34 (Example 15) (66 mg, 0.2 mmol) was dissolved in ethanol (4 mL) containing KOH (40 mg, 0.6 mmol) and refluxed (32 h). The equilibrium point (96/4, cis/trans) was reached after 8 h. The reaction was quenched by pouring into saturated NaCl (10 mL), extracted with CHCl$_3$ (2×5 mL), dried, and evaporated to give 65.6 mg (98%) of the mixture. Preparative GC (240° C.) gave 41 mg (63% recovery) of pure cis-34 as a colorless oil: NMR δ 7.2 (m, 1H), 6.9 (m, 3H), 3.95 (m, 4H), 3.50 (s, 3H), 2.70 (s, 3H); IR 1620, 1603, 1578 cm$^{-1}$; mass spectrum m/e (rel intensity) 331 (19), 99 (35), 55 (100). Anal. Calcd for C$_{19}$H$_{25}$NO$_4$: C, 68.9; H, 7.6; N, 4.2. Found: C, 68.9; H, 7.6; N, 4.4 trans-34 has a GC retention time (237° C.) of 2.6 min while that for cis-34 is 3.4 min. Analysis of the isomeric ratio obtained in the cyclization of 32 (Example 12) to 33 (Example 13) was by hydrolysis of the crude cyclized material [as per 33 (Example 13) to 9] and ketalization [as per trans-9 (Example 14) to 34] without purification of intermediates. GC of the crude ketals gave the isomeric ratios in Table 1 of the specification.

EXAMPLE 17 cis-1,6-Dioxo-4a-(3'-methoxyphenyl)-2-methyldecahydroisoquinoline (cis-9)

Ketal cis-34 (Example 16) (20 mg, 0.06 mmol) was dissolved in 1:1 THF/1 N H$_2$SO$_4$ (2 mL) and stirred for 60 h. Ether (2 mL) and saturated NaCl (1 mL) were added, the aqueous phase washed with ether (1 mL), and the combined organic phases washed with saturated NaCl (2 mL), dried, and evaporated to yield 17 mg (99%) of pure cis-9: NMR δ 7.30 (t,J=9 Hz, 1H), 6.9 (m, 3H), 3.78 (s, 3H), 7.87 (s, 3H), 2.63 (s, 2H); IR 1712, 1634, 1603, 1580 cm$^{-1}$; mass spectrum m/e (rel intensity) 287 (32), 218 (26), 55 (100). Anal. Calcd for C$_{17}$H$_{21}$NO$_3$: C, 71.0; H, 7.4; N, 4.9. Found: C, 71.0; H, 7.4; N, 4.9.

EXAMPLE 18

Reduction of trans-34 of Example 15

The general procedure involved dissolving trans-34 (0.1–0.2 mmol) in THF (2–4 mL), adding 500 mol % of either LiAlH$_4$ (1.0 M in THF), B$_2$H$_6$ (1.0 M in THF), AlH$_3$ (0.65 M in THF), or DiBAL (1.98 M in hexane), and stirring for 30 min at various temperatures. Reactions were monitored as described below for trans-35 (Example 19) and by NMR.

A. AlH$_3$, 0° C. Reduction and isolation gave a 57/43 ratio of amine trans-35 and enamine 38: NMR 5.96 (s, 1H) and 2.60 (s, 3H); IR 1673 cm$^{-1}$ [compared to the known phenyl compound: NMR δ 5.97 (s, 2.42 (s, 3H): IR 1671 cm$^{-1}$]. Resubmission of the crude reduction prouct to the reaction conditions resulted in reisolation of the same mixture.

B. LiAlH$_4$; AlH$_3$, 78° C. The THF solution of trans-34 (Example 15) at −78° C. was treated with LiAlH$_4$, stirred for 30 s, then treated with AlH$_3$. After stirring for 30 min, isolation gave a mixture consisting of 61% of amine trans-35 (Example 19), 13% of enamine 38, and 26% of trans-34 (Example 15).

C. AlH₃; LiAlH₄, −78° C. The procedure was as in B, but with AlH₃ added before LiAlH₄. Isolation gave an 82/18 amine trans-35 (Example 19) to enamine 38 ratio with no starting material present.

D. LiAlH₄. No reaction occurred at 0° C., 25° C., or at reflux.

E. B₂H₆. No reaction occurred at 25° C. At reflux a complex mixture was obtained.

F. DiBAL, 0° C., After isolation there was obtained amine trans-35 (Example 19) and enamine 38 in a 10/90 ratio.

EXAMPLE 19 trans-6,6-Ethylenedioxy-4a-(3'-methoxyphenyl)-2-methyl-decahydroisoquinoline (trans-35)

Ketal amide trans-34 (Example 15) (450 mg, 1.35 mmol) in THF (25 mL, anhydrous) in a dry ice/acetone bath was treated with AlH₃ (4.05 mmol in THF, 0.65 M) and stirred for 1 min. LiAlH₄ (6.75 mmol in THF, 1.01 M) was added, and the solution was warmed gradually to 0° C. and maintained at that temperature for 60 min. Excess hydride was decomposed by the addition of 1:1 THF/H₂O (125 μL) followed by 3.33 N NaOH (325 μL). The reaction solution was poured into Et₂O (50 mL) and saturated NaCl (10 mL) along with two washings of the salts with Et₂O (5 mL). Drying and evaporating yielded 426 mg (100%) of crystalline material which by NMR was 25% enamine 38 and 75% trans-35. This residue was dissolved in methanol (25 mL) and hydrogenated at 50 psi H₂ in the presence of 5% Rh/Al₂O (130 mg) for 10 h. Filtration and evaporation gave 441 mg of material which was recrystallized (benzene/hexane, 1:2), returning 182 mg (42%) of pure trans-35, mp 124.5°–126° C. Chromatography (SiO₂ 1–10% NH₄OH/C₂H₅OH) of the mother liquor afforded 177 mg (41%) of pure trans-35 (83% overall): NMR δ 7.3–6.9 (m, 3H), 6.68 (dt, J=2 Hz, 7.1 H), 3.88 (s, 3H), 4.0–3.2 (m, 7), 2.25 (s, 3H); IR 1605, 1580 cm⁻¹; mass spectrum m/e (rel intensity) 317 (80), 316 (45), 99 (21), 71 (100), 70 (62). Anal. Calcd for C₁₉H₂₇NO₃: C, 71.9; H, 8.6; N, 4.4. Found: C, 71.7; H, 8.5; N, 4.5.

EXAMPLE 20 cis-6,6-Ethylenedioxy-4a-(3'-methoxyphenyl)-2-methyldecahydroisoquinoline (cis-35)

Crude ketal amide cis-34 (Example 16) (360 mg, 1.09 mmol, 96% cis, 4% trans) in THF (10 mL) at 0° C. was treated with AlH₃ (5.50 mmol in THF, 0.65 M) and the cloudy solution stirred for 60 min. Isolation as for the trans amine yielded 362 mg of crude cis-35. Chromatography (SiO₂, 1–10% NH₄OH/C₂H₅OH) returned 264 mg (73%) of pure amine ketal cis-35: NMR δ 7.2–6.9 (m, 3H), 6.71 (bd,J=8 Hz, 1H), 4.1–3.6 (m, 7H), 3.88 (s, 3H), 2.12 (s, 3H); IR 1603, 1577 cm⁻¹; mass spectrum m/e (rel intensity) 317 (99), 272 (82), 99 (20), 71 (100), 70 (63). Anal. Calcd for C₁₉H₂₇N₃: C, 71.9; H, 8.6; N, 4.4. Found: C, 71.8; H, 8.5; N, 4.3.

EXAMPLE 21 cis- and trans-4a-(3'-Methoxyphenyl)-2-methyl-6-oxodecahydroisoquinolines (cis- and trans-36)

Trans. The ketal amine trans-35 (Example 19) (170 mg, 0.536 mmol) was dissolved in 1 N H₂SO₄ (15 mL) and stirred for 26 h at 25° C. Basification (2 N NaOH) and extraction with CHCl₃ (3×10 mL), followed by washing the organic phase with saturated NaCl (10 mL), drying and evaporating yielded 145 mg (99%) of pure amino ketone trans-36 which was recrystallized from benzene/hexane, 1/1: mp 94°–95° C.; NMR δ 7.4–6.9 (m, 3H), 6.70 (dt, J=2, 7 Hz, 1H), 3.77 (s, 3H), 2.32 (s, 3H); IR 1706, 1603, 1580 cm⁻¹; mass spectrum m/e (rel intensity) 273 (31), 272 (21), 71(93), 70 (100). Anal. Calcd for C₁₇H₂₃NO₂: C, 74.7; H, 8.5; N, 5.1. Found: C, 74.6; H, 8.3; N, 5.1.

Cis. In a manner exactly as above ketal amine cis-35 (Example 20) (263 mg, 0.83 mmol) was converted into the ketone amine cis-36 (233 mg) as an oil which was homogeneous by GC: NMR δ 7.4–6.6 (m, 4H), 3.78 (s, 3H), 2.35 (s, 3H); IR 1701, 1598, 1577 cm⁻¹; mass spectrum m/e (rel intensity) 273 (68), 71 (100), 70 (87). Anal. Calcd for C₁₇H₂₃NO₂: C, 74.7; H, 8.5; N, 5.1. Found: C, 74.8; H, 8.5; N, 5.1

EXAMPLE 22 trans-4a-(3'-Methoxyphenyl)-2-methyldecahydroisoquinoline (trans-37a)

A solution containing H₂NNH₂.H₂O (900 mg, 18 mmol), KOH (105 mg, 1.6 mmol), and the ketone trans-36 (Example 21) (136 mg, 0.5 mmol) in diethylene glycol (1.5 mL) was refluxed for 1 h and then distilled until the distillate reached 175° C. The solution was then refluxed for an additional 1 h, cooled to 25° C., diluted with H₂O (20 mL, pH 12), and extracted with benzene (3×10 mL). The organic layer was washed with 1 N NaOH (5 mL), H₂O (5 mL), and saturated NaCl (5 mL), dried, and evaporated to yield 16.9 mg (13%) of trans-37a: NMR δ 7.4–7.0 (m, 3H), 6.72 (m, 1H), 3.82 (s, 3H), 2.24 (s, 3H); IR 1600, 1580 cm⁻¹; mass spectrum m/e (rel intensity) 259 (58), 258 (51), 151 (40), 150 (27), 71 (100), 70 (58). Anal. Calcd for C₁₇H₂₅NO₂: C, 78.7; H, 9.7; N, 5.4. Found: C, 78.7; H, 9.7; N, 5.4. A picrate was prepared, mp 165°–166° C.

EXAMPLE 23 trans-4a-(3'-Hydroxyphenyl)-2-methyldecahydroisoquinoline (trans-37b)

The combined alkaline aqueous layers above were adjusted to pH 8 and extracted with benzene (3×15 mL). The combined organic phase was washed with NaCl (10 mL), dried, and evaporated to give 82 mg (67%) of phenol trans-37b which was recrystallized from CHCl₃/hexane, 8/1: mp 210°–211.5° C.; NMR δ 7.03 (m, 4H), 6.47 (d,J=7 Hz, 1H), 2.27 (s, 3H); IR 3670, 3590, 1592 (sh), 1582 cm⁻¹; mass spectrum m/e (rel intensity) 245 (68), 244 (69), 151 (39), 150 (21), 71 (100), 70 (77). Anal. Calcd for C₁₃H₂₃NO: C, 78.2; H, 9.4; N, 5.7. Found: C, 78.1; H, 9.4; N. 5.7.

EXAMPLE 24 cis-4a-(3'-Methoxyphenyl)-2-methyldecahydroisoquinoline (cis-37a)

In exactly the same manner as for the trans ketone (Example 21), 199 mg (0.73 mmol) of ketone cis-36 was converted to amine cis-37a (41 mg, 22%): NMR δ 7.29 (t,J=8 Hz, 1H), 7.04 (m, 2H), 6.74 (dt, J=2,8 Hz, 1H), 3.82 (s, 3H), 2.24 (s, 3H); IR 1600, 1580 cm⁻¹; mass spectrum m/e (rel intensity) 259 (50), 258 (37), 151 (29), 150 (14), 71 (100), 70 (58). Anal. Calcd for C₁₇H₂₅NO: C, 78.7; H, 9.7; N, 5.4. Found: C, 78.6; H, 9.7; N, 5.4. A picrate was prepared and was an oil.

EXAMPLE 25 cis-4a-(3'-Hydroxyphenyl)-2-methyldecahydroisoquinoline (cis-37b)

The combined alkaline aqueous layers above were adjusted to pH 8 and extracted with benzene (3×20 mL). The combined organic phase was washed with saturated NaCl (10 mL), dried, and evaporated to give 87 mg (50%) of phenol cis-37b, which was distilled [bp 160° C. (0.1 mm)]: NMR δ 7.5–6.5 (m, 5H), 2.28 (s, 3H); IR 3663, 1595 cm$^{-1}$ (b); mass spectrum m/e (rel intensity) 245 (67), 244 (60), 151 (34), 150 (17), 71 (100), 70 (79). Anal. Calcd for $C_{16}H_{23}NO$: C, 78.2; H, 9.4; N, 5.7. Found: C, 78.0; H, 9.4; N, 5.7.

EXAMPLE 26 trans-6,6-Dimethoxy-4a-(3'-methoxyphenyl)-2-methyldecahydroisoquinoline (44)

Ketone trans-36 (Example 21) (3.215 g, 117 mmol), trimethyl orthoformate (5.3 g, 50 mmol), sulfuric acid (1.88 mL, 36 N, 34 mmol), and $CH_3OH$ (350 mL) were refluxed for 20 min, an equal portion of the orthoformate was added, and reflux was continued for 20 min. The cooled solution was evaporated to 100 mL, cooled, and poured into $H_2O$ (300 mL) containing NaOH (4 g, 100 mmol) and $CHCl_3$ (200 mL). The separated aqueous layer was washed with $CHCl_3$ (3×50 mL), and the combined organic phases were washed with saturated NaCl (50 mL), dried, and evaporated to give 3.80 g (100%) of ketal 44. A small portion was distilled [135°–140° C. (0.1 mm)] although the crude material was used in all subsequent reactions: NMR δ 7.16 (m, 3H), 6.68 (dt, J=2,7 Hz, 1H), 3.84 (s, 3H), 3.14 (s, 3H), 2.42 (s, 3H), 2.27 (s, 3H); IR 1601, 1580 cm$^{-1}$; mass spectrum m/e (rel intensity) 319 (10), 287 (68), 272 (100), 71 (25), 70 (41). Anal. Calcd for $C_{19}H_{29}NO_3$: C, 71.4; H, 9.1; N, 4.4. Found: C, 71.6; H, 9.1; N, 4.4.

EXAMPLE 27 trans-$\Delta^5$-and-$\Delta^6$-6-Methoxy-4a-(3'-methoxyphenyl)-2-methyloctahydroisoquinolines (46a and 45a)

The crude ketal 44 (Example 26) (3.8 g, 11.7 mmol) was dissolved in toluene (450 mL), treated with pyridine (11.1 g, 140 mmol) and $POCl_3$ (5.73 g, 37.4 mmol), and refluxed for 2 h at which time a clear brown oil had separated. The cooled (10° C.) vigorously stirred emulsion was rapidly treated with cold (0° C.) 1 N NaOH (224 mL), then shaken until no oil remained. The separated aqueous layer was washed with benzene (2×50 mL), the combined organic phases were washed with saturated NaCl (50 mL), dried and evaporated, and the residue was distilled [140°–150° C. (0.1 mm)] giving 3.07 g (91%) of pure enol ethers (NMR revealed a C-5/C-7 vinyl proton ratio of 13/87; the $W_{1/2}$ for C-5 H was 2 Hz and for C-7 H was 7 Hz): NMR δ 7.27 (m, 3H), 6.68 (dt, J=2,7 Hz, 1H), 3.80 (s, 3H), 2.30 (s, 3H); $\Delta^5$: 4.85 (s, 1H), 3.47 (s, 3H); $\Delta^6$, 4.70 (s, 1H), 3.40 (s, 3H); IR 1664, 1601, 1580 cm$^{-1}$; mass spectrum m/e (rel intensity) 287 (63), 286 (23), 273 (22), 272 (100), 71 (30), 70 (45). Anal. Calcd for $C_{18}H_{25}NO_2$: C, 75.2; H, 8.8; N, 4.9. Found: C, 75.0; H, 8.7; N, 4.9.

EXAMPLE 28

Enol Acetates 45b and 46b

Ketone trans-36 (Example 21) (45 mg, 0.15 mmol) and acetic anhydride (2 mL) containing $TsOH.H_2O$ (34 mg, 0.20 mmol) were heated at reflux for 8 h and evaporated. The residue was dissolved in $CHCl_3$ (15 mL), washed with saturated $NaHCO_3$, dried, and evaporated to give 37 mg (78%) of 45b/46b in a 79/21 ratio: NMR δ 7.4–6.8 (m, 3H), 6.73 (bd,J=7 Hz, 1H), 3.82 (s, 3H), 2.30 (s); the $\Delta^5$ enol acetate 46b had δ 5.62 (s, $W_{1/2}$=4 Hz, 1H), 2.08 (s, 3H); the $\Delta^7$ isomer 45b had δ 5.37 (s, $W_{1/2}$=7 Hz, 1H). 2.02 (s, 3H).

EXAMPLE 29 trans-5-and-7-Bromo-6,6-dimethoxy-4a-(3'-methoxyphenyl)-2-methyldecahydroisoquinoline (48 and 47)

The enol ether mixture (3.02 g, 10.5 mmol) at 0° C. in $CH_3OH$ (65 mL) was treated with N-bromoacetamide (1.52 g, 11.02 mmol) in $CH_3OH$ (65 mL) and allowed to stand for 12 h. The $CH_3OH$ was evaporated and benzene (100 mL) and 2 N NaOH (50 mL) were added, then shaken until no oil remained. The separated organic layer was washed with benzene (2×50 mL), and the combined organic phases were washed with 2 N NaOH (15 mL), $H_2O$ (15 mL), and saturated NaCl (25 mL), then dried and evaporated to yield 4.32 g (~100%) of a mixture of 47 and 48. NMR revealed the C-5 H/C-7 H ratio to be 13/87 with $W_{1/2}$ of 4 Hz for C-5 H and 6 Hz for C-7 H. Pure 5-bromo compound 48 may be obtained via chromatography after HBr elimination from 48 to either 39 or 49 (Example 30 and Example 31, respectively): NMR δ 7.0 (m, 4H), 4.72 (s, 1H), 3.84 (s, 3H), 3.14 (s, 3H), 2.55 (s, 3H), 2.25 (s, 3H); IR 1601, 1580 cm$^{-1}$; mass spectrum m/e (rel intensity) 399 (4), 397 (4), 319 (29), 318 (100), 71 (30), 70 (55); bp 150°–155° C. (0.1 mm). Anal. Calcd for $C_{19}H_{28}NO_3Br$: C, 57.3; H, 7.1; N, 3.5. Found: C, 57.5; H, 7.1; N, 3.6.

The 7-bromo isomer 47 exhibits the following NMR: δ 7.05 (m, 3H), 6.66 (dt,J=2,7 Hz, 1H), 3.84 (s, 3H), 3.14 (s, 3H), 2.30 (s, 3H), 2.25 (s, 3H).

EXAMPLE 30 trans-$\Delta^7$-6,6-Dimethoxy-4a-(3'-methoxyphenyl-2-methyloctahydroisoquinoline (39)

The crude mixture of bromo ketals 47 and 48 (Example 29) (4.32 g, 10.5 mmol), 1,5-diazabicyclo[4.3.0]non-5-ene (DBN, 6.52 g, 52.5 mmol), and $Me_2SO$ (36.9 g, 472 mmol) were heated at 120° C. for 15 h, cooled, and shaken thoroughly with benzene (200 mL), $H_2O$ (500 mL) and saturated NaCl (50 mL). The separated aqueous layer was washed with benzene (2×100 mL), and the combined organic phases were washed with $H_2O$ (90 mL), saturated NaCl (10 mL), $H_2O$ (2×50 mL), and saturated NaCl (100 mL), dried and evaporated to yield 3.46 g (~100%) of a mixture of bromo ketal 18 (Example 29) and ketal 39. Chromatography ($SiO_2$, $CHCl_3/CH_3OH$, 9/1, 0.25%, $NH_4OH$) returned 2.26 g (68%) of pure 39 and 318 mg (7.5%) of pure 48. An intermediate fraction (454 mg, 12%) was also collected. The trans $\Delta^7$ ketal 39 was crystallized from benzene/hexane: mp 122°–123° C.; NMR δ 7.4–6.8 (m, 4H), 5.98 (d,J=10 Hz, 1H), 5.77 (bd,J=10 Hz, 1H), 3.84 (s, 3H), 3.18 (s, 3H), 2.73 (s, 3H), 2.25 (s, 3H), IR 1605, 1582 cm$^{-1}$; mass spectrum m/e (rel intensity) 317 (2), 286 (14), 285 (47), 270 (38), 257 (46), 254 (25), 150 (100), 71 (52), 70 (26). Anal. Calcd for $C_{19}H_{27}NO_3$: C, 71.9; H, 8.6; N, 4.4. Found: C, 72.0; H, 8.6; N, 4.4.

EXAMPLE 31

$\Delta^{8(8a)}$-6,6-Dimethoxy-4a-(3'-methoxyphenyl)-2-methyloctahydroisoquinoline (49)

A. The crude mixture of ketals 47 and 48 (Example 29) (943 mg, 2.37 mmol), potassium tert-butoxide (610 mg, 5.0 mmol), and Me$_2$SO (16 mL) was heated at 60° C. for 4 h. Isolation and chromatography as for the $\Delta^7$ isomer yielded 66 mg (7%) recovered 48 and 557 mg (74%) of pure 49: NMR $\delta$ 7.27 (t, J=7 Hz, 1H), 7.0–6.6 (m, 3H), 5.84 (t, J=4 Hz, 1H), 3.84 (s, 3H), 3.25 (s, 3H), 2.40 (s, 3H), 2.22 (s, 3H); IR 1600, 1577 cm$^{-1}$; mass spectrum m/e (rel intensity) 317 (6), 287 (7), 286 (13), 285 (38), 178 (59), 146 (100).

A methiodide was prepared in CH$_3$OH with excess CH$_3$I and recrystallized from ethyl acetate/ethanol, mp 191° C. dec. Anal. Calcd for C$_{20}$H$_{30}$NO$_3$I: C, 52.3; H, 6.6; N, 3.0. Found: C, 52.1; H, 6.7; N, 3.0.

B. The $\Delta^7$ ketal 39 (31.7 mg, 0.1 mmol) was converted by the procedure in part A above to 49 (25 mg, 79%).

EXAMPLE 32

$\Delta^6,\Delta^{8(8a)}$-Methoxy-4a-(3'-methoxyphenyl)-2-methylhexahydroisoquinoline (8)

A. The $\Delta^{8(8a)}$ ketal 49 (Example 31) (556 mg, 1.75 mmol), potassium tert-butoxide (830 mg, 7 mmol), and Me$_2$SO (17.5 mL) were heated at 105° C. for 90 min. followed by isolation as for the formation of 49. The crude 363 mg after chromatography (SiO$_2$, CHCl$_3$/CH$_3$OH, 9/1, 0.25% NH$_4$OH) returned 102 mg (20%) of 8 as a dark oil: bp 165°–170° C. (0.1 mm); NMR $\delta$ 7.4–6.6 (m, 4H), 6.07 (dd, J=2.6 Hz, 1H), 4.87 (dd, J=2.6 Hz, 1H), 3.82 (s, 3H), 3.45 (s, 3H), 2.30 (s, 3H); IR 1653, 1602, 1580 cm$^{-1}$; mass spectrum m/e (rel intensity) 285 (100), 284 (46), 270 (27), 254 (25), 178 (60), 71 (26), 70 (11). Anal. Calcd for C$_{18}$H$_{23}$NO$_2$: C, 75.7; H, 8.1; N, 4.9. Found: C, 75.4; H, 8.2; N, 4.7.

B. The $\Delta^7$ ketal 39 (Example 30) (422 mg, 1.33 mmol) was dissolved in toluene (55 mL) and treated with pyridine (1.76 g, 16 mmol) and POCl$_3$ (650 mg, 4.25 mmol), then refluxed for 30 min. after which time a clear brown oil had separated. Isolation was as for the enol ethers 45a and 46a (Example 27) and distillation returned 279 mg (74%) of an oil, bp 125°–135° C. (0.05 mm), consisting of two materials, 8 (85%) and 55 (15%), indistinguishable chromatographically. NMR of 55 had $\delta$ 5.89 (t, J=4 Hz, 1H), 4.17 (s, 1H). The mixture of dienes was used in subsequent oxidation and cycloaddition reactions.

EXAMPLE 33

$\Delta^{8(8a)}$-4a-(3'-Methoxyphenyl)-2-methyl-6-oxooctahydroisoquinoline (41)

Ketal 49 (Example 31) (50 mg, 0.158 mmol) was dissolved in 2 mL of 3 N acetic acid and stirred for 4 h. Basification (pH 8.5), extraction with CHCl$_3$ (2×5 mL), drying, and evaporation gave 29 mg (68%) of 41 as an oil. Attempted distillation resulted in decomposition and 41 failed to form a crystalline methiodide: NMR $\delta$ 7.27 (t, J=7 Hz, 1H), 6.77 (m, 3H), 5.96 (m, 1H), 3.78 (s, 3H), 2.27 (s, 3H); IR 1715, 1595, 1578 cm$^{-1}$; mass spectrum m/e (rel intensity) 271 (100), 215 (43), 164 (48), 71 (55), 70 (41). C$_{17}$H$_{18}$NO$_2$ requires 271.1572; found 271.1563.

EXAMPLE 34 trans-$\Delta^7$-4a-(3'-Methoxyphenyl)-2-methyl-6-oxooctahydroisoquinoline (40)

Ketal 39 (Example 30) (476 mg, 1.5 mmol) in benzene (30 mL) was shaken three times with 0.2 N HClO$_4$ (30, 10, 10 mL), and the aqueous solution allowed to stand for 30 min. Basification to pH 8.5 extraction with CHCl$_3$ (3×10 mL), drying, and evaporation gave 410 mg (100%) of a mixture of ketones. After dissolution in benzene (25 mL) the ketones were extracted into NaHSO$_3$/Na$_2$SO$_3$, pH 7. The aqueous bisulfite was cooled (0° C.), basified to pH 8.5, and extracted with benzene to give after removal of solvent 67 mg (16%) of pure 41 (Example 33). The remaining bisulfite solution was further basified to pH 12 and extracted with benzene using mechanical shaking, the benzene layer being separated and replaced by a fresh layer at intervals of 2, 2, 4, and 10 h. Drying and evaporation of the combined organic extract gave ketone 40 (285 mg, 69%): mp 78°–80° C.; NMR $\delta$ 7.4–7.0 (m, 1H), 7.00 (dd, J=2.10 Hz, 1H), 6.75 (m, 3H), 5.95 (dd, J=3.5, 10 Hz, 1H), 3.78 (s, 3H), 2.30 (s, 3H); IR 1672, 1597, 1588 cm$^{-1}$; mass spectrum m/e (rel intensity) 271 (100), 228 (28), 215 (43), 214 (31), 164 (48), 122 (35), 71 (22), 70 (14). A methiodide was prepared in CH$_3$OH and recrystallized from acetone, mp 201° C. dec. Anal. Calcd for C$_{18}$H$_{24}$NO$_2$I: C, 52.3; H, 5.8; N, 3.4. Found: C, 52.2; H, 5.8; N, 3.4.

EXAMPLE 35 cis-$\Delta^7$-4a-(3'-Methoxyphenyl)-2-methyl-6-oxooctahydroisoquinoline (42)

The trans $\alpha,\beta$-unsaturated ketone 40 (Example 34) (350 mg, 1.29 mmol), CH$_3$ONa (2.58 mL of 0.5 M in CH$_3$OH, 1.29 mmol), and CH$_3$OH (35 mL) were stirred for 13 h at 25° C. poured into H$_2$O (100 mL) and extracted with CH$_2$Cl$_2$ (4×25 mL), and the combined organic phases were washed with saturated NaCl (20 mL), dried, and evaporated to yield 350 mg (100%) of a 65/35 mixture of 42 and 41 (Example 33). Separation was exactly as for the mixtures of 40 and 41 (Examples 34 and 33 above) giving 112 mg (32%) of 41 and 199 mg (57%) of 42: NMR $\delta$ 7.26 (t, J=8 Hz, 1H), 7.1–6.6 (m, 4H), 5.98 (dd, J=1.5, 10 Hz, 1H), 3.80 (s, 3H), 2.30 (s, 3H); IR 1672, 1595, 1580 cm$^{-1}$; mass spectrum m/e (rel intensity) 271 (19), 243 (12), 200 (15), 71 (100), 70 (20). C$_{17}$H$_{21}$NO$_2$ requires 271.1572; found 271.1561.

EXAMPLE 36 trans-6$\alpha$-Hydroxy-4a$\alpha$-(3'-methoxyphenyl)-2-methyldecahydroisoquinoline (50)

To ketone trans-36 (Example 21) (25 mg, 0.090 mmol) in acetic acid (1 mL) was added PtO$_2$ (10 mg) and the mixture hydrogenated at 50 psi H$_2$ for 60 min. Filtration and evaporation gave a residue which was dissolved in H$_2$O (10 mL), basified (2 N NaOH), and extracted with CHCl$_3$ (3×10 mL), followed by washing the organic phase with saturated NaCl, drying, and evaporation to give 25 mg (100%) of a single isomer which was crystalized from hexane: mp 117°–117.5° C.; TLC (CH$_3$OH/CHCl$_3$, 3/20, 1% NH$_4$OH), R$_f$ 0.52; NMR $\delta$ 7.4–7.0 (m, 3H), 6.70 (dt, J=2, 8 Hz, 1H), 3.97 (m, W$_{1/2}$=6 Hz, 1H), 3.80 (s, 3H), 2.22 (s, 3H), IR 3571, 3413, 1605, 1577 cm$^{-1}$; mass spectrum m/e (rel intensity) 275 (100), 204 (40), 71 (84), 70 (72). Anal. Calcd for C$_{17}$H$_{25}$NO$_2$: C, 74.1; H, 9.1; N, 5.1. Found: C, 73.9; H, 9.0; N, 5.1.

EXAMPLE 37 trans-6β-Hydroxy-4aα-(3'-methoxyphenyl)-2-methyl-decahydroisoquinoline (51)

A. Ketone trans-36 (Example 21) (55 mg. 0.202 mmol) and 2-propanol (157 mg, 2.62 mmol, anhydrous) in toluene (2 mL, anhydrous) at reflux were treated with sodium (24.1 mg, 1.05 mmol) in five small portions, waiting for each portion to dissolve. After the last portion had reacted, TLC (CH$_3$OH/CHCl$_3$, 3/20, 1% NH$_4$OH) showed only two materials, R$_f$ 0.52 and 0.35. The reaction mixture was cooled, mixed with benzene (10 mL), washed with H$_2$O (5 mL) and saturated NaCl (5 mL), dried, and evaporated to yield 55 mg of an oil. Preparative TLC (as above) returned 10 mg (18%) of 50 and 20 mg (36%) of 51 which was distilled: bp 125°–130° C. (0.08 mm); NMR δ 7.4–6.9 (m, 3H), 6.68 (dt, J=2, 8 Hz, 1H), 3.80 (s, 3H), 3.5–3.7 (m, W$_{1/2}$=20 Hz, 1H), 2.23 (s, 3H); IR 3571, 3425, 1601, 1580 cm$^{-1}$; mass spectrum m/e (rel intensity) 275 (100), 274 (62), 71 (72), 70 (96). Anal. Calcd for C$_{17}$H$_{25}$NO$_2$: C, 74.1; H, 9.1; N, 5.1. Found: C, 74.0; H, 9.1; N, 5.1.

B. Sodium borohydride reduction of trans-36 (Example 21) as per reduction of cis-36 below gave 50/51 in a ratio of 70/30 by GC.

EXAMPLE 38 cis-6α-Hydroxy-4aα-(3'-methoxyphenyl)-2-methyl-decahydroisoquinoline (54) and cis-6β-Hydroxy-4aα-(3'-methoxyphenyl)-2-methyl-decahydroisoquinoline (53)

A. To ketone cis-36 (Example 21) (27.3 mg, 0.1 mmol) in acetic acid (2 mL) was added PtO$_2$ (10 mg) and the mixture was hydrogenated at 60 psi H$_2$ for 3 h. Isolation as for 50 (Example 36) gave 28 mg of an oil shown by TLC (as above) to be two compounds (R$_f$ of 53, 0.49, and R$_f$ of 54, 0.42). NMR revealed that the 53/54 ratio was approximately 1/2 by inspection of the NCH$_3$ absorptions.

B. To ketone cis-36 (Example 21) (100 mg, 0.364 mmol) in ethanol was added NaBH$_4$ (42 mg, 1.1 mmol) in three portions over a 1-h period. After a further 1 h at 25° C., the reaction mixture was poured into H$_2$O (20 mL) and extracted with CH$_2$Cl$_2$ (3×10 mL), and the organic phase was washed with saturated NaCl (10 mL), dried and evaporated to an oil. NMR showed a 53/54 ratio of 3/2. Preparative TLC returned 53 (45 mg, 45%) and 54 (35 mg, 35%) and distillation furnished analytical materials.

53: bp 130°–135° C. (0.08 mm); NMR δ 7.4–6.9 (m, 3H), 6.71 (dt, J=2, 7 Hz, 1H), 3.80 (s, 3H), 4.3–3.2 (m, 1H), 2.34 (s, 3H); IR 3571, 3436, 1608, 1850 cm$^{-1}$; mass spectrum m/e (rel intensity) 275 (100), 274 (47), 71 (88), 70 (68). Anal. Calcd for C$_{17}$H$_{25}$NO$_2$: C, 74.1; H, 9.1; N, 5.1. Found: C, 73.9; H, 9.1; N, 5.0.

54: mp 95°–97° C. from benzene; bp 130°–135° C. (0.08 mm); NMR δ 7.28 (t, J=8 Hz, 1H), 7.02 (m, 2H), 6.75 (bd, J=8 Hz, 1H), 3.84 (s, 3H), 4.3–3.2 (m, 1H), 2.14 (s, 3H); IR 3571, 3413, 1595, 1572 cm$^{-1}$; mass spectrum m/e (rel intensity) 275 (40), 274 (26), 71 (100), 70 (66). Anal. Calcd for C$_{17}$H$_{25}$NO$_2$: C, 74.1; H, 9.1; N, 5.1. Found: C, 74.3; H, 9.1; N, 5.1.

EXAMPLE 39

Reduction of Δ$^{8(8a)}$-4a-(3'-Methoxyphenyl)-2-methyl-6-oxooctahydroisoquinoline (41)

Δ$^{8(8a)}$-6-Hydroxy-4-(3'-methoxyphenyl)-2-methyl-decahydroisoquinoline. To ketone 41 (72 mg, 0.292 mmol) in ethanol (4 mL) at 0° C. was added NaBH$_4$ (63 mg, 1.6 mmol) in two portions at 15-min intervals. The solution was warmed to 25° C. and stirred for 60 min, poured into H$_2$O (30 mL), extracted with CH$_2$Cl$_2$ (3×20 mL), dried, and evaporated to yield an oil which was chromatographed (TLC grade SiO$_2$, CHCl$_3$/CH$_3$OH, 9/1, 0.5% NH$_4$OH) to give homogeneous material (TLC, GC) (34 mg, 47%): bp 130° C. (0.1 mm); NMR δ 7.28 (t, J=7.5 Hz, 1H), 6.82 (m, 3H), 5.83 (m, 1H), 4.2–3.4 (m, 1H), 3.80 (s, 3H), 2.13 (bs, 3H); IR 3584, 2967, 2841, 2793, 1605, 1580 cm$^{-1}$; mass spectrum m/e (rel intensity) 273 (100), 272 (25), 271 (26), 256 (22), 255 (23), 228 (29), 167 (36), 166 (84). Anal. Calcd for C$_{17}$H$_{23}$NO$_2$: C, 74.7; H, 8.5; N, 5.1. Found: C, 74.6; H, 8.5; N, 5.0.

To the alcohol (27 mg, 0.1 mmol) in CH$_3$OH (2 mL) was added PtO (10 mg) and the mixture shaken under 55 psi H$_2$ for 2 h. Filtration and evaporation gave 27 mg of a material which was two major components. Chromatography (as above) returned 10 mg of trans alcohol 50 and 5 mg of trans alcohol 51 (Examples 36 and 37).

EXAMPLE 40 trans-Δ$^7$-6α-and 6β-Hydroxy-4aα-(3'-methoxyphenyl-2-methyloctahydroisoquinolines (7 and 52)

The trans ketone 40 (Example 34) (200 mg, 0.736 mmol) in THF (10 mL) was treated with 0.65 M AlH$_3$ THF (3.4 mL, 2.21 mmol) and then stirred for 30 min. all at 0° C. THF/H$_2$O (1/1, 1.1 mL) was added followed by 3.3 N NaOH (3.0 mL) and ether (20 mL). The separated aqueous layer was washed with benzene (10 mL), and the combined organic phases were washed with saturated NaCl (10 mL), dried, and evaporated to give 185 mg of a colorless oil. Chromatography (TLC grade SiO$_2$, CH$_3$OH/CHCl$_3$, 9/1, 0.25–1% NH$_4$OH) returned first 112 mg (56%) of trans-Δ$^7$-6α-hydroxy-4aα-(3'-methoxyphenyl)-2-methyloctahydroisoquinoline (7): NMR δ 7.5–6.5 (m, 3H), 6.72 (dt, J=2.7 Hz, 1H), 5.85 (distorted dd, J=11 Hz, 2H), 4.2–4.0 (bs, W$_{\frac{1}{2}}$=11 Hz, 1H), 3.78 (s, 3H), 2.22 (s, 3H); IR 3571, 2933, 2857, 2817, 1603, 1580 cm$^{-1}$; mass spectrum m/e (rel intensity) 273 (95), 202 (98), 71 (100), 70 (60): bp 125° C. (0.1 mm). Anal. Calcd for C$_{17}$H$_{23}$NO$_2$: C, 74.7; H, 8.5; N, 5.1. Found: C, 74.5; H, 8.4; N, 5.1.

Next eluted was 9 mg (4.5%) of ketone trans-36 (Example 21) identified by spectral and chromatographic comparisons.

Lastly was obtained 62 mg (31%) of trans-Δ$^7$-6β-hydroxy-4aα-(3-methoxyphenyl)-2-methyloctahydroisoquinoline (52): NMR δ 7.4–6.6 (m, 4H), 5.69 (dd, J=10 Hz, 2H), 3.9–3.4 (bs, 1H), 3.78 (s, 3H), 2.17 (s, 3H); IR 3636, 1603, 1580 cm$^{-1}$; mass spectrum m/e (rel intensity) 273 (55), 256 (18), 255 (21), 71 (100), 70 (37); bp 130° C. (0.1 mm). Anal. Calcd for C$_{17}$H$_{23}$NO$_2$: C, 74.7; H, 8.5; N, 5.1. Found: C, 74.5; H, 8.4; N, 5.2.

Allylic alcohol 7, when reduced as described for the α,β-unsaturated alcohol obtained from 41 (Example 33, 39), returned only 50 (Example 36). Reduction of 52 in the same manner yielded 51 (Example 37).

EXAMPLE 41 trans-Δ⁷-6α-Hydroxy-4aα-(3'-hydroxyphenyl)-2-methyloctahydroisoquinoline (6)

A solution of potassium thioethoxide/DMF was prepared as follows. To DMF (30 mL degassed by freeze/thaw) was added potassium tert-butoxide (1.5 g, 13.4 mmol), and the suspension was degassed and flushed thoroughly with argon. Ethanethiol (1.22 mL, 1.64 mmol) was added and the butoxide dissolved leaving a clear, colorless solution. Ether 7 (40 mg, 0.15 mmol) in DMF (1 mL) was thoroughly degassed and placed under argon. The thioethoxide solution (1 mL, 0.44 mmol) was added, and the solution was heated at 150° C. for 10 h, cooled, poured into $H_2O$ (20 mL), the pH adjusted to 14, and extracted with $CHCl_3$ (3×4 mL) after which the pH was lowered to 8 and the solution was extracted with 9/1 $CHCl_3$/2-propanol (4×4 mL). The combined organic phases were washed with saturated NaCl (10 mL), dried, and evaporated to a mixture of phenols (33 mg). Trituration of the residue with hot benzene and cooling returned 24 mg (60%) of pure 6 as an amorphous solid: NMR δ 7.3–6.5 (m, 4H), 5.84 (distorted dd, J=10 Hz, 2H), 4.07 (m, 1H), 2.29 (s, 3H); IR 3550, 3247 (b), 1582 cm⁻¹; mass spectrum m/e (rel intensity) 259 (100), 258 (32), 188 (91), 71 (94), 70 (59). Sublimation gave mp 199°–203° C. Anal. Calcd for $C_{16}H_{21}NO_2$: C, 74.1; H, 8.2; N, 5.4. Found: C, 73.8; H, 8.1; N, 5.4.

EXAMPLE 42 cis-Δ⁷-6α- and cis-Δ⁷-6β-Hydroxy-4aα-(3'-methoxyphenyl)-2-methyloctahydroisoquinolines (10 and 11).

The cis ketone 42 (Example 35) (171 mg, 0.63 mmol) in toluene (6.3 mL, 0° C.) was treated rapidly with diisobutylaluminum hydride (1.26 mmol), 2 M in hexane, 0° C.) and stirred for 30 min. and $CH_3OH$ (0.25 mL) was added, followed by 2 N NaOH (10 mL) and benzene (10 mL). The separated aqueous layer was washed with benzene (10 mL), and the combined organic phases were dried and evaporated to yield 168 mg of a clear glass. Chromatography (TLC grade $SiO_2$, $CHCl_3CH_3OH$, 9/1 0.25% $NH_4OH$) returned in order of elution 4.2 mg (2.5%) of 42 (Example 35), 17.2 mg (9%) of ketone cis-36 (Example 21), and 75.2 mg (44%) of cis-Δ⁷-6α-hydroxy-4aα-(3'-methoxyphenyl)-2-methyloctahydroisoquinoline (10): NMR δ 7.30 (dd, J=7,9 Hz, 1H), 6.97 (m, 2H), 6.75 (bd, J=8 Hz, 2H), 5.84 (dd, J=10 Hz, 2H), 4.27 (t, 1H), 3.82 (s, 3H), 2.18 (s, 3H); IR 3571, 2924, 2857, 2817, 1601, 1580 cm⁻¹; mass spectrum m/e (rel intensity) 273 (39), 202 (53), 200 (21), 71 (100), 70 (40): mp 133°–135° C. from benzene. Anal. Calcd for $C_{17}H_{23}NO_2$: C, 74.7; H, 8.5; N, 5.1. Found: C, 74.6; H, 8.5; N, 5.1.

Eluted next was 21.6 mg (12.5%) of an intermediate fraction, then 19.3 mg (11%) of cis-Δ⁷-6β-hydroxy-4aα-(3'-methoxyphenyl)-2-methyloctahydroisoquinoline (11): NMR δ 7.25 (t, J=8 Hz, 1H), 6.81 (m, 3H), 5.85 (dd, J=4,9 Hz, 1H), 5.57 (d, J=9 Hz, 1H), 3.82 (s, 3H), 3.9–4.5 (m, 1H), 2.32 (s, 3H): IR 3570, 2933, 2849, 2807, 1601, 1582 cm⁻¹; mass spectrum m/e (rel intensity) 273 (27), 71 (100), 70 (45); bp 125°–130° C. (0.1 mm). Anal. Calcd for $C_{17}H_{23}NO_2$: C, 74.7; H, 8.5; N, 5.1. Found: C, 74.5; H, 8.5; N, 5.0.

Reduction of 10 with $PtO_2/H_2/CH_3OH$ as for 7 (Example 40) gave only 54 (Example 38). Reduction of 11 under these conditions afforded 53 (Example 38).

EXAMPLE 43

Δ⁷-8a-Hydroxy-4a-(3'-methoxyphenyl)-2-methyl-6-oxooctahydroisoquinolines (57 and 58)

To the mixture of dienes 8 (Example 32) and 55 (85/15) (120 mg, 0.42 mmol) in acetic acid (3 mL) was added trifluoroacetic acid (60 mg, 0.53 mmol). m-Chloroperbenzoic acid (62 mg, 0.37 mmol) was added and the solution heated (95° C.) for 15 min., cooled, treated with additional peracid (41.2 mg, 0.24 mmol), and heated again (95° C.) for 20 min. The dark solution was cooled (5° C.), added to $H_2O$ (10 mL), and basified (pH 12), then extracted with $CHCl_3$ (3×20 mL); the combined organic phases were dried and evaporated, affording 105 mg of an oil. Chromatography (TLC grade $SiO_2$, $CHCl_3/CH_3OH$, 9/1 0.1% $NH_4OH$) gave three compounds. Eluted first was 52 mg (43%) of a Δ⁷-8a-hydroxy ketone: NMR δ 7.20 (t, J=8Hz, 1H), 6.95 (d, J=10 Hz, 1H), 6.9–6.9 (m, 3H), 6.03 (d, J=10 Hz, 1H), 3.79 (s, 3H), 2.29 (s, 3H); IR 3356, 1675, 1603, 1580 cm⁻¹; mass spectrum m/e (rel intensity) 287 (7), 259 (9), 71 (100), 70 (9). Anal. Calcd for $C_{17}H_{21}NO_3$: C, 71.0; H, 7.4; N, 4.9. Found: C, 70.9; H, 7.3; N, 4.9.

Eluted next was 9 mg (7%) of the epimeric Δ⁷-8a-hydroxy ketone: NMR δ 7.22 (t, J=8 Hz, 1H), 6.97 (d, J=10 Hz, 1H), 6.8–6.6 (m, 3H), 6.15 (d, J=10 Hz, 1H), 3.79 (s, 3H), 2.28 (s, 3H); IR 3356, 1686, 1605, 1580 cm⁻¹. $C_{17}H_{21}NO_3$ requires 287.1521; found, 287.1514.

Obtained last was 19.5 mg (16%) of the N-oxide 59: NMR δ 7.26 (t, J=8 Hz, 1H), 6.95 (d, J=10 Hz, 1H), 6.9–6.7 (m, 3H), 5.82 (d, J=10 Hz, 1H), 3.77 (s, 3H), 3.14 (s, 3H); IR 3650, 3600–2300 (bs), 1678, 1605, 1580 cm⁻¹; mass spectrum m/e (rel intensity) 303 (0.36), 302 (0.36), 301 (0.64), 287 (17), 43 (100).

EXAMPLE 44

Diels-Alder Reactions of 8 (Example 32) with:

A. Ethyl Acrylate. The mixture of dienes 8 and 55 (85/15, 28.5 mg, 0.1 mmol) was dissolved in ethyl acrylate (5 mL) and heated at reflux for 15 h, cooled, evaporated, and chromatographed ($SiO_2$, $CHCl_3/CH_3OH$, 9/1 0.1% $NH_4OH$). The recovered dienes (25 mg, 88%) were still present in a 85/15 ratio. From the reaction in a sealed tube at 170° C., starting material was recovered in 40% yield after chromatography.

B. Methyl vinyl ketone (MVK), as in A, with MVK at reflux for 9 h returned starting material (64%).

C. Dimethyl Acetylenedicarboxylate (DMAD). The dienes (55 mg, 0.19 mmol) and DMAD (35 mg, 0.38 mmol) were dissolved in toluene (0.5 mL) and stirred for 9.5 h at 25° C. The solution was evaporated and chromatographed twice ($SiO_2$, $CHCl_3/CH_3OH$, 9/1, 0.1% $NH_4OH$, then with $CHCl_3$) to return 33 mg (39%) of triene 63 [NMR revealed 63 to be a mixture of the fumarate (10–20%) and the maleate (80–90%) based on the multiplicity of the enamine proton, the N-methyl, and the O-methyl region]: NMR δ 7.79 (t, J=8 Hz, 1H), 6.85 (m, 3H), 6.29 (d, J=10 Hz, 1H), 5.87 (broadened d, J=10 Hz, 1H), 5.64 (bs, 0.1H), 5.31 (s, 0.9H), 4.89 (s, 1H), 4.70 (d, J=8 Hz), and 4.49 (broadened d, J=8Hz), total of 2H, 3.9–3.4 (complex, four large singlets at 3.92, 3.82, 3.65, 3.62 with two small singlets at 3.55 and 3.47, total 12H), 3.4–2.9 (m, 2H), 2.85 and 2.73 (singlets, ~4/1, total 3H), 2.5–1.9 (m, 2H); IR 1739, 1653, 1577 cm$^{-1}$; mass spectrum m/e (rel intensity) 427 (26), 426 (27), 368 (40), 269 (33), 254 (47), 228 (57), 227 (100), 226 (27), 225 (72). $C_{24}H_{29}NO_6$ requires 427.1995; found 427.1991. UV (CH$_3$OH) λ c max 274 nm (ε 20 800).

D. N-Phenylmaleimide. The dienes (37 mg, 0.135 mmol) and N-phenylmaleimide (25.6 mg, 0.148 mmol) in toluene were heated at 110° C. for 12 h and cooled and the solvent was evaporated. The NMR showed that little starting materials had been consumed and was nearly identical with an NMR of the starting mixture. The reaction mixture was again subjected to the same conditions and after 170 h neither starting material remained. Both NMR and TLC (CHCl$_3$ or CHCl$_3$/CH$_3$OH, 9/1 0.1% NH$_4$OH) revealed several materials. Chromatography on SiO$_2$ gave no identifiable compounds.

We claim:

1. In a process of preparing 4a-aryldecahydroisoquinolines the steps consisting essentially of the conversion of nipecotates to substituted methylenepiperidone and carboxylic ring formation according to the following reaction system:

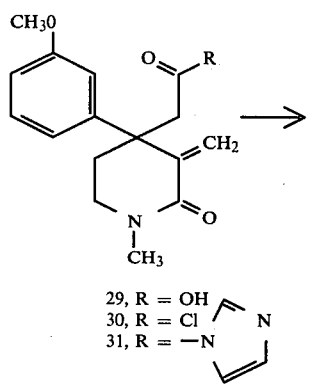

29, R = OH
30, R = Cl
31, R = —N⟨imidazole⟩ wherein 4-carboxymethyl-4-(3'-methoxyphenyl)-1-methyl-3-methylene-2-piperidone (29) is converted to an imidazolide (31) by the action of carbonyldiimidazole in CHCl$_3$/THF and subsequently with the magnesium enolate of tert-butyl hydrogen malonate to produce tert-butyl 4-[4'-[4'-(3''-methoxy-phenyl)-1'-methyl-3'-methylene-2'-oxopiperidyl]]-3-oxobutyrate (32) and this material 32 is cyclized by an alkali metal methanolate dissolved in methanol to tert-butyl 1,6-dioxo-4a-(3'-methoxyphenyl)-2-methyl-decahydroisoquinoline-7-carboxylate (33) and subsequently 33 is treated with trifluoroacetic acid in benzene and subsequent recovery by recrystallization from a benzene-hexane mixture to produce trans 1,6-dioxo-4a-(3'-methoxyphenyl)-2-methyl-decahydroisoquinoline (9).

2. In the process according to claim 1 wherein the material 32 is cyclized using CH$_3$ONa/CH$_3$OH.

* * * * *